(12) United States Patent
Jesudason et al.

(10) Patent No.: US 7,122,680 B2
(45) Date of Patent: Oct. 17, 2006

(54) 3-SUBSTITUTED OXINDOLE $\beta_3$ AGONSISTS

(75) Inventors: Cynthia Darshini Jesudason, Indianapolis, IN (US); Daniel Jon Sall, Greenwood, IN (US); Freddie Craig Stevens, Indianapolis, IN (US); John Arnold Werner, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/970,194

(22) Filed: Oct. 21, 2004

(65) Prior Publication Data

US 2005/0054713 A1 Mar. 10, 2005

Related U.S. Application Data

(62) Division of application No. 10/399,206, filed as application No. PCT/US01/50666 on Oct. 26, 2001, now Pat. No. 6,825,220.

(60) Provisional application No. 60/306,793, filed on Jul. 20, 2001, provisional application No. 60/247,304, filed on Nov. 10, 2000.

(51) Int. Cl.
C07D 209/04 (2006.01)
C07D 209/32 (2006.01)
C07D 401/12 (2006.01)
C07D 237/02 (2006.01)
A61K 31/44 (2006.01)

(52) U.S. Cl. .................. 548/452; 548/456; 546/268.1; 544/239; 514/337; 514/256; 514/412

(58) Field of Classification Search ................ 548/452, 548/456; 546/268.1; 544/239; 514/337, 514/256, 412
See application file for complete search history.

(56) References Cited

U.S. PATENT DOCUMENTS

| 4,276,304 | A |   | 6/1981  | Ikezaki et al. |
|-----------|---|---|---------|----------------|
| 4,642,309 | A | * | 2/1987  | Michel et al. ............ 514/269 |
| 4,826,847 | A |   | 5/1989  | Michel et al. |
| 5,808,080 | A |   | 9/1998  | Bell et al. |
| 5,977,154 | A |   | 11/1999 | Bell et al. |
| 6,011,048 | A |   | 1/2000  | Mathvink et al. |

FOREIGN PATENT DOCUMENTS

| DE | 2830884 | 1/1979 |
|----|---------|--------|
| EP | 166331 | 1/1986 |
| EP | 221414 | 5/1987 |
| EP | 236624 | 9/1987 |
| EP | 611003 | 8/1994 |
| EP | 678511 | 10/1995 |
| EP | 764640 | 3/1997 |
| EP | 0827746 | 3/1998 |
| GB | 1549945 | 8/1979 |
| WO | WO 95/29159 | 11/1995 |
| WO | WO 97/10825 | 3/1997 |
| WO | WO 97/46556 | 12/1997 |
| WO | WO 98/04526 | 2/1998 |
| WO | WO 98/9625 | 3/1998 |
| WO | WO 98/32753 | 7/1998 |
| WO | WO 00/40560 | 7/2000 |
| WO | WO 00/44721 | 8/2000 |
| WO | WO 01/7026 | 2/2001 |
| WO | WO 01/35947 | 5/2001 |
| WO | WO 01/36412 | 5/2001 |
| WO | WO 01/53298 | 7/2001 |

OTHER PUBLICATIONS

English abstract Caplus DN 122:389427. Lee An-Rong et al 1995.*
Lee, et al., *J. Het. Chem.*, 32(1):1-11, 1995.
Mathvink, *Bioorganic & Medicinal Chemistry Letters*, 9(13):1869-1874, 1999.
Shuker, AJ, et al; *Tetrahedron Letters*; 38(35):6149-6152, 1997.
Weber, et al; *Bioorganic & medicinal Chemistry Letters*; 8(9):1101-1106, 1998.
Weber AE, et al; *Bioorganic & Medicinal Chemistry Letters*; 8(16):2111-2116, 1998.

* cited by examiner

*Primary Examiner*—Rita Desai
(74) *Attorney, Agent, or Firm*—John C. Demeter; Gilbert T. Voy

(57) ABSTRACT

The present invention relates to a $\beta_3$ adrenergic receptor agonist of formula I:

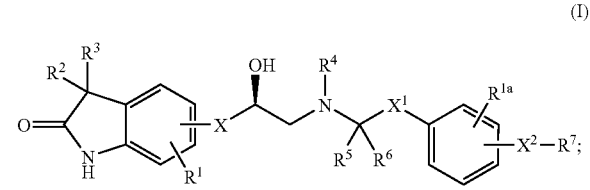

(I)

or a pharmaceutical salt thereof; which is useful for treating Type II diabetes and/or obesity.

4 Claims, No Drawings

3-SUBSTITUTED OXINDOLE β₃ AGONSISTS

This application is a divisional under 35 U.S.C. § 121 of U.S. patent application Ser. No. 10/399,206, filed Apr. 11, 2003 now U.S. Pat. No. 6,825,220 which claims the benefit under 35 U.S.C. § 120 of International Application No. PCT/US01/50666 filed Oct. 26, 2001, which claims the benefit under 35 U.S.C. § 119(e) of U.S. Ser. No.'s 60/247,304, filed Nov. 10, 2000 and 60/306,793, filed Jul. 20, 2001.

FIELD OF INVENTION

The present invention is in the field of medicine, particularly in the treatment of Type II diabetes and obesity. More specifically, the present invention relates to $\beta_3$ adrenergic receptor agonists useful in the treatment of Type II diabetes and obesity.

BACKGROUND OF THE INVENTION

The current preferred treatment for Type II, non-insulin dependent diabetes as well as obesity is diet and exercise, with a view toward weight reduction and improved insulin sensitivity. Patient compliance, however, is usually poor. The problem is compounded by the fact that there are currently no approved medications that adequately treat either Type II diabetes or obesity.

One therapeutic opportunity that has recently been recognized involves the relationship between adrenergic receptor stimulation and anti-hyperglycemic effects. Compounds that act as $\beta_3$ receptor agonists have been shown to exhibit a marked effect on lipolysis, thermogenesis and serum glucose levels in animal models of Type II (non-insulin dependent) diabetes.

The $\beta_3$ receptor, which is found in several types of human tissue including human fat tissue, has roughly 50% homology to the $\beta_1$ and $\beta_2$ receptor subtypes yet is considerably less abundant. Stimulation of the $\beta_1$ and $\beta_2$ receptors can cause adverse effects such as tachycardia, arrhythmia, or tremors. An agonist that is selective for the $\beta_3$ receptor over the $\beta_1$ and $\beta_2$ receptors is, therefore, more desirable for treating Type II diabetes or obesity relative to a non-selective agonist.

However, recent studies have suggested the presence of an atypical beta receptor associated with atrial tachycardia in rats (*Br. J. of Pharmacol.*, 118:2085–2098, 1996). In other words, compounds that are not agonists of the $\beta_1$ and $\beta_2$ receptors can still modulate tachycardia through activation of a yet to be discovered $\beta_4$ or through some other unknown pathway.

A large number of publications have appeared in recent years reporting success in discovery of agents that stimulate the $\beta_3$ receptor. For example, U.S. Pat. No. 5,786,356 discloses $\beta_3$ agonists of the formula:

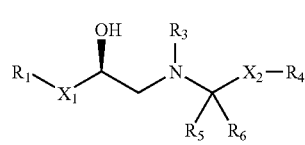

wherein:
$R_1$ can be, among other things, a moiety of the formula:

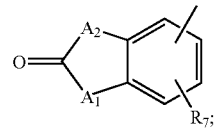

$A_1$ and $A_2$ can be, among other things, NH, $CH_2$, $NCH_3$, or $NCH_2CH_3$; and
$R_4$ can be, among other things, a moiety of the formula:

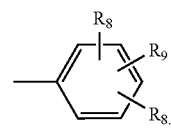

Despite these recent developments, there remains a need to develop a selective $\beta_3$ receptor agonist which has minimal agonist activity against the $\beta_1$ and $\beta_2$ receptors and which displays a minimal propensity to cause atrial tachycardia.

SUMMARY OF INVENTION

The present invention relates to a compound of formula I:

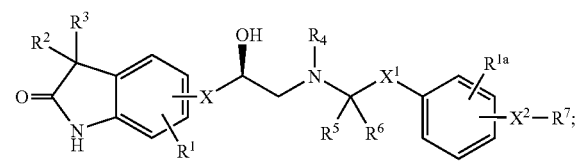

wherein:
$R^1$ is H, CN, halo, $C_1$–$C_6$ alkyl, $C_1$–$C_4$ haloalkyl, $CO_2R^8$, $CONHR^8$, $NHCOR^8$, $NHR^8$, $OR^8$, $SR^8$, $SOR^8$, $SO_2R^8$ or $SO_2NHR^8$;
$R^{1a}$ is H, halo or $C_1$–$C_6$ alkyl;
$R^2$ is H, $C_1$–$C_6$ alkyl or benzyl;
$R^3$ is $C_1$–$C_6$ alkyl or benzyl;
or $R^2$ and $R^3$ combine with the carbon to which each are attached to form a $C_3$–$C_7$ carbocyclic ring; provided that if $R^3$ is $C_2$–$C_6$ alkyl or benzyl, then $R^2$ must be hydrogen;
$R^4$ is H or $C_1$–$C_6$ alkyl;
$R^5$ and $R^6$ are independently H or $C_1$–$C_6$ alkyl; or
$R^5$ and $R^6$ combine with the carbon to which each are attached to form a $C_3$–$C_6$ carbocyclic ring;
or $R^6$ combines with $X^1$, the carbon to which both are attached, and the phenyl group to which $X^1$ is attached to form a moiety selected from the group consisting of:

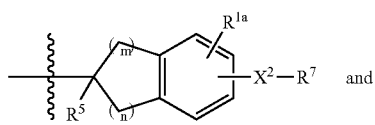

and

-continued

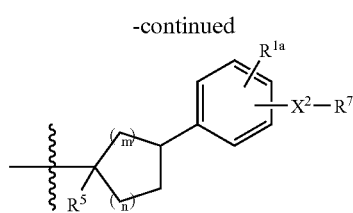

wherein:
m and n are independently 0, 1, 2, or 3 provided that the sum of n+q is $\leq 5$ and that $R^5$ is H;
$R^7$ is hydrogen, optionally substituted phenyl or optionally substituted heterocycle;
$R^8$ is H or $C_1$–$C_6$ alkyl;
X is $OCH_2$, $SCH_2$ or a bond; and
$X^1$ is a bond or a $C_1$–$C_5$ divalent hydrocarbon moiety; and
$X^2$ is O, S, NH, $NHSO_2$, $SO_2NH$, $CH_2$ or a bond;

or a pharmaceutical salt thereof.

The present invention also relates to processes for preparing, as well as novel pharmaceutical formulations containing, a compound of formula I. In another embodiment, the pharmaceutical formulations of the present invention may be adapted for use in treating Type II diabetes and obesity and for agonizing the $\beta_3$ receptor.

The present invention also relates to methods for treating Type II diabetes and obesity, as well as a method for agonizing the $\beta_3$ receptor employing a compound of formula I.

In addition, the present invention relates to a compound of formula I for use in treating Type II diabetes and obesity as well as a compound of formula I for use in agonizing the $\beta_3$ receptor. The present invention is further related to the use of a compound of formula I for the manufacture of a medicament for treating Type II diabetes and obesity as a well as for agonizing the $\beta_3$ receptor.

The present invention is also related to a compound of formula II:

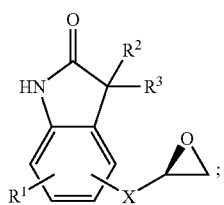

which is useful as an intermediate to prepare a compound of formula I.

DETAILED DESCRIPTION

For the purposes of the present invention, as disclosed and claimed herein, the following terms are defined below.

The term "halo" represents fluoro, chloro, bromo, or iodo.

The term "$C_1$–$C_6$ alkyl" represents a straight, branched or cyclic hydrocarbon moiety having from one to six carbon atoms, e.g., methyl, ethyl, n-propyl, isopropyl, cyclopropyl, n-butyl, isobutyl, sec-butyl, t-butyl, cyclobutyl, pentyl, cyclopentyl, hexyl, cyclohexyl and the like. The term "$C_1$–$C_4$ alkyl" refers specifically to methyl, ethyl, n-propyl, isopropyl, cyclopropyl, n-butyl, isobutyl, sec-butyl, t-butyl and cyclobutyl. A "$C_1$–$C_4$ haloalkyl" group is a $C_1$–$C_4$ alkyl moiety substituted with up to six halo atoms, preferably one to three halo atoms. An example of a haloalkyl group is trifluoromethyl. A "$C_1$–$C_6$ alkoxy" group is a $C_1$–$C_6$ alkyl moiety connected through an oxy linkage. A "$C_1$–$C_4$ alkoxy" group is a $C_1$–$C_4$ alkyl moiety connected through an oxy linkage.

The term "divalent hydrocarbon moiety" refers to a straight or branched chain of carbon atoms that may optionally have one or more points of unsaturation. Thus, a hydrocarbon diradical according to the present invention includes alkylene, alkenylene and alkylidene moieties. Examples include but are not intended to be limited to methylene, ethylene, propylene, butylene, $-CH(CH_3)CH_2-$, $-CH(C_2H_5)CH_2-$, $-CH(CH_3)CH(CH_3)-$, $-CH_2C(CH_3)_2-$, $-CH_2CH(CH_3)CH_2-$, $-C(CH_3)_2CH_2-$, $-CH=CHCH_2-$, $-CH=CH-$, $-C=CCH_2-$, and the like.

The term "optionally substituted" as used herein means an optional substitution of one to three, preferably one or two groups independently selected from oxo, nitro, cyano, phenyl, benzyl, halo, $C_1$–$C_6$ alkyl, $C_1$–$C_4$ haloalkyl, $COR^9$, $NR^{10}R^{10}$, $NR^{10}COR^9$, $NR^{10}SO_2R^{11}$, $OR^{10}$, $OCOR^9$, $OSO_2R^{11}$, $SR^{10}$, $SOR^{11}$, $SO_2R^{11}$ or $SO_2NR^{10}R^{10}$; wherein $R^9$ is H, $C_1$–$C_6$ alkyl, phenyl, benzyl, $C_1$–$C_4$ haloalkyl, $NR^{10a}R^{10a}$ or $OR^{10a}$;

$R^{10}$ and $R^{10a}$ are independently H, $C_1$–$C_6$ alkyl or phenyl; or when two $R^{10}$ or $R^{10a}$ groups are attached to the same nitrogen atom, said $R^{10}$ or $R^{10a}$ groups, together with the nitrogen to which they are attached, may combine to form a piperidine, pyrrolidine, hexamethyleneimine or morpholine ring; and $R^{11}$ is $C_1$–$C_6$ alkyl or phenyl.

The term "heterocycle" represents a stable, saturated, partially unsaturated, fully unsaturated or aromatic 5 or 6 membered ring, said ring having from one to four heteroatoms that are independently selected from the group consisting of sulfur, oxygen, and nitrogen. The heterocycle may be attached at any point which affords a stable structure. Representative heterocycles include 1,3-dioxolane, 4,5-dihydro-1H-imidazole, 4,5-dihydrooxazole, furan, imidazole, imidazolidine, isothiazole, isoxazole, morpholine, oxadiazole, oxazole, oxazolidinedione, oxazolidone, piperazine, piperidine, pyrazine, pyrazole, pyrazoline, pyridazine, pyridine, pyrimidine, pyrrole, pyrrolidine, tetrazole, thiadiazole, thiazole, thiophene and triazole.

The term "suitable solvent" refers to any solvent, or mixture of solvents, inert to the ongoing reaction that sufficiently solubilizes the reactants to afford a medium within which to effect the desired reaction.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The preferred patient of treatment is a human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "preventing", "prevention of", "prophylaxis", "prophylactic" and "prevent" are used herein interchangeably and refer to reducing the likelihood that the recipient of a compound of formula I will incur or develop any of the pathological conditions, or sequela thereof, described herein.

As used herein, the term "effective amount" means an amount of a compound of formula I that is capable of treating conditions, or detrimental effects thereof, described herein or that is capable of agonizing the $\beta_3$ receptor.

The term "selective $\beta_3$ receptor agonist" means a compound that displays preferential agonism of the $\beta_3$ receptor over agonism of the $\beta_1$ or $\beta_2$ receptor. Thus, $\beta_3$ selective compounds behave as agonists for the $\beta_3$ receptor at lower concentrations than that required for similar agonism at the $\beta_1$ and $\beta_2$ receptors. A $\beta_3$ selective compound also includes compounds that behave as agonists for the $\beta_3$ receptor and as antagonists for the $\beta_1$ and $\beta_2$ receptors.

The term "pharmaceutical" when used herein as an adjective means substantially non-deleterious to the recipient patient.

The term "formulation", as in pharmaceutical formulation, is intended to encompass a product comprising the active ingredient(s) (compound of formula I), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier.

The term "unit dosage form" refers to physically discrete units suitable as unitary dosages for human subjects and other non-human animals, each unit containing a predetermined quantity of active material calculated to produce the desired therapeutic effect, in association with a suitable pharmaceutical carrier.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt. Such salts include the salicylate, sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and like salts. Preferred acid addition salts include the hydrochloride and glycolate salts.

It is recognized that various stereoisomeric forms of a compound of formula I exist. The compounds may be prepared as racemates and can be conveniently used as such. Therefore, the racemates, individual enantiomers, diastereomers, or mixtures thereof form part of the present invention. Unless otherwise specified, whenever a compound is described or referenced in this specification all the racemates, individual enantiomers, diastereomers, or mixtures thereof are included in said reference or description.

It is also recognized that various tautomeric forms of a compound of formula I may exist, and all tautomeric forms are part of the present invention. Unless otherwise specified, whenever a compound is described or referenced in this specification all tautomeric forms, or mixtures thereof, are included in said reference or description.

PREFERRED COMPOUNDS OF THE INVENTION

Certain compounds of the invention are particularly interesting and are preferred. The following listing sets out several groups of preferred compounds. It will be understood that each of the listings may be combined with other listings to create additional groups of preferred compounds.

a) $R^1$ is H, CN, halo, $C_1$–$C_4$ alkyl, $C_1$–$C_4$ haloalkyl, $CO_2R^8$, $CONHR^8$, $NHCOR^8$, $NHR^8$, $OR^8$, $SR^8$, $SOR^8$, $SO_2R^8$ or $SO_2NHR^8$;

b) $R^1$ is H, methyl, ethyl, $CF_3$, chloro or fluoro;

c) $R^1$ is H, methyl, chloro or fluoro;

d) $R^1$ is H or fluoro;

e) $R^1$ is H;

f) $R^{1a}$ is H, halo or $C_1$–$C_4$ alkyl;

g) $R^{1a}$ is H, methyl, ethyl, chloro or fluoro;

h) $R^{1a}$ is H, methyl, chloro or fluoro;

i) $R^{1a}$ is H;

j) $R^2$ is H and $R^3$ is methyl;

k) $R^2$ and $R^3$ are both methyl;

l) $R^2$ and $R^3$ combine with the carbon to which each are attached to form a pentacylic or hexacyclic ring;

m) $R^2$ and $R^3$ combine with the carbon to which each are attached to form a propacylic or butacyclic ring;

n) $R^2$ and $R^3$ are both methyl or combine with the carbon to which each are attached to form a pentacylic ring;

o) $R^2$ and $R^3$ combine with the carbon to which each are attached to form a pentacylic ring;

p) $R^4$ is H or $C_1$–$C_4$ alkyl;

q) $R^4$ is H;

r) $R^5$ is H or $C_1$–$C_4$ alkyl;

s) $R^6$ is H or $C_1$–$C_4$ alkyl;

t) $R^5$ is H or methyl;

u) $R^6$ is H or methyl;

v) $R^5$ and $R^6$ are both methyl;

w) $R^7$ is hydrogen, phenyl or heterocycle wherein said phenyl or heterocycle is optionally substituted one to three times independently with hydroxy, oxo, nitro, phenyl, benzyl, $C_1$–$C_4$ alkoxy, $COR^8$, $NHCO(C_1$–$C_4$ alkyl), NHCO(phenyl), NHCO(benzyl), $OCO(C_1$–$C_4$ alkyl), $OCO_2R^8$ and $OCONR^8R^8$;

x) $R^7$ is selected from hydrogen, optionally substituted phenyl, pyridyl, thienyl and furanyl;

y) $R^7$ is phenyl, pyridyl, thienyl or furanyl wherein said $R^7$ moieties are substituted one to three times with fluoro, chloro, cyano, hydroxy, methyl, ethyl, trifluoromethyl, methoxy, ethoxy, amino, $CO_2CH_3$, $CO_2CH_2CH_3$, $CONR^8R^8$, $SCH_3$, $SCH_2CH_3$, $SOCH_3$, $SOCH_2CH_3$, $SO_2CH_3$ or $SO_2CH_2CH_3$;
z) $R^7$ is phenyl, pyridyl, thienyl or furanyl wherein said $R^7$ moieties are substituted one to three times with fluoro, cyano, hydroxy, methyl, ethyl, methoxy, ethoxy, amino, carboxymethyl, carboxyethyl, $CONH_2$, $CO_2CH_3$, $CO_2CH_2CH_3$, $CONH_2$, $SCH_3$, $SCH_2CH_3$, $SOCH_3$, $SOCH_2CH_3$, $SO_2CH_3$ or $SO_2CH_2CH_3$;
aa) $R^7$ is phenyl, pyridyl, thienyl or furanyl wherein said $R^7$ moieties are substituted one to three times with fluoro, amino, $CO_2CH_3$, $CO_2CH_2CH_3$, cyano, $CONH_2$, $SO_2CH_3$ or $SO_2CH_2CH_3$;
bb) $R^7$ is phenyl, pyridyl, pyridazinyl or pyrimidinyl wherein said $R^7$ moieties are optionally substituted once or twice with chloro, cyano, $CONH_2$ or $CO_2CH_3$;
cc) $R^7$ is phenyl, pyridyl, thienyl or furanyl wherein said $R^7$ moieties are substituted once with cyano or $CONH_2$;
dd) $R^7$ is phenyl or pyridyl wherein said $R^7$ moieties are substituted once with cyano or $CONH_2$;
ee) $R^7$ is pyridyl substituted once with cyano or $CONH_2$;
ff) $R^7$ is 5-cyano or 5-carboxamido-pyrid-2-yl;
gg) $R^7$ is 4-cyano or 4-carboxamido-phenyl;
hh) $R^7$ is 3-cyano or 3-carboxamido-pyrid-2-yl;
ii) $R^7$ is 2-cyano or 2-carboxamido-phenyl;
jj) $R^8$ is H or $C_1$–$C_4$ alkyl;
kk) $R^8$ is hydrogen;
ll) X is connected to the indole ring system at the 4-position of said system;
mm) X is $OCH_2$;
nn) $X^1$ is a bond, methylene or ethylene;
oo) $X^1$ is methylene;
pp) $X^2$ is at the para-position relative to $X^1$;
qq) $X^2$ is a bond or O;
rr) $X^2$ is O;
ss) the compound of formula I is an acid addition salt;
tt) the compound of formula I is the hydrochloride salt;
uu) the compound of formula I is the glycolate salt.

Synthesis

The compound of formula I may be prepared as described in the following Schemes and Examples.

The reaction of Scheme 1 may be carried out under conditions appreciated in the art for the amination of epoxides. For example, the epoxide of formula II may be combined with an amine of formula III in a lower alcohol, dimethylformamide, dimethylsulfoxide, or acetone, preferably ethanol, isopropanol, n-butanol or t-butanol, at room temperature to the reflux temperature of the reaction mixture, preferably between 40° C.–90° C. The reaction may also be carried out under conditions generally described in Atkins, et al., *Tet. Let.*, 27:2451, 1986. These conditions include mixing the reagents in the presence of trimethylsilyl acetamide in a polar aprotic solvent such as acetonitrile, dimethylformamide, acetone, dimethylsulfoxide, dioxane, diethylene glycol dimethyl ether, tetrahydrofuran, or other polar aprotic solvents in which the reagents are soluble.

The epoxide starting materials employed in Scheme 1 may be prepared by techniques recognized and appreciated by one skilled in the art. See, e.g., references cited below in the Preparations section for representative and/or analogous procedures for preparing the epoxides of formula II. To illustrate, epoxides of formula II, where X is $OCH_2$ or $SCH_2$ and where $R^2$ and $R^3$ combine with the carbon to which each are attached to form a $C_3$–$C_7$ carbocyclic ring, may be prepared according to the procedure detailed in Scheme 2 wherein $R^{12}$ is chloro, bromo or iodo, X' is O or S, and X" is $OCH_2$ or $SCH_2$ and p is 0–4.

In addition, epoxides of formula II, where X is $OCH_2$ or $SCH_2$ and where $R^2$ and $R^3$ do not combine with the carbon to which each are attached to form a carbocyclic ring, may be prepared according to the procedure detailed in Scheme 3 below where $R^{2'}$ is $C_1$–$C_6$ alkyl or benzyl.

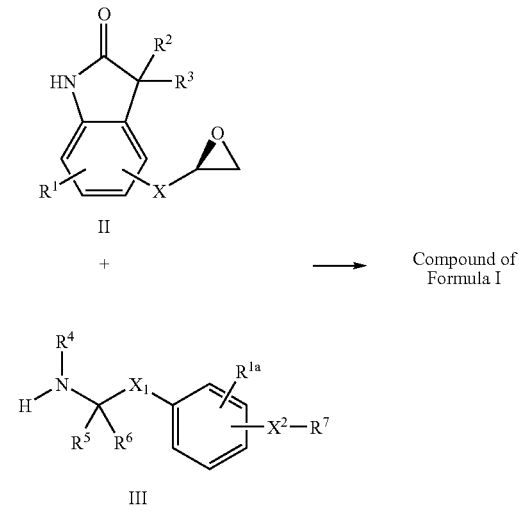

Scheme 1

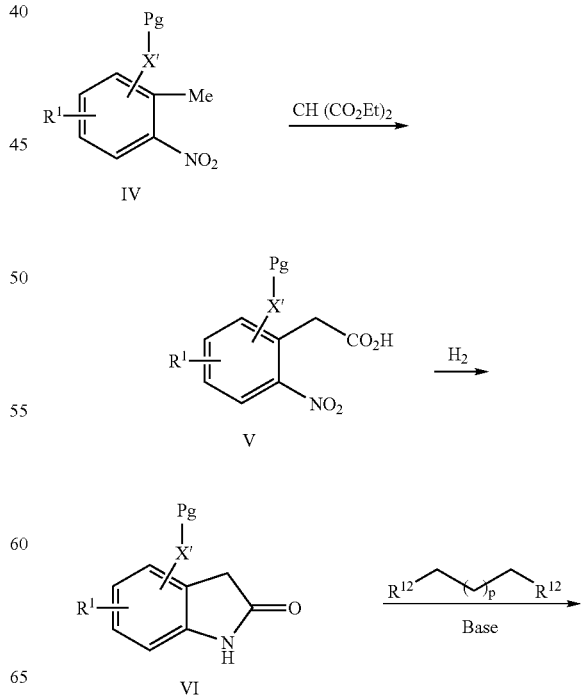

Scheme 2

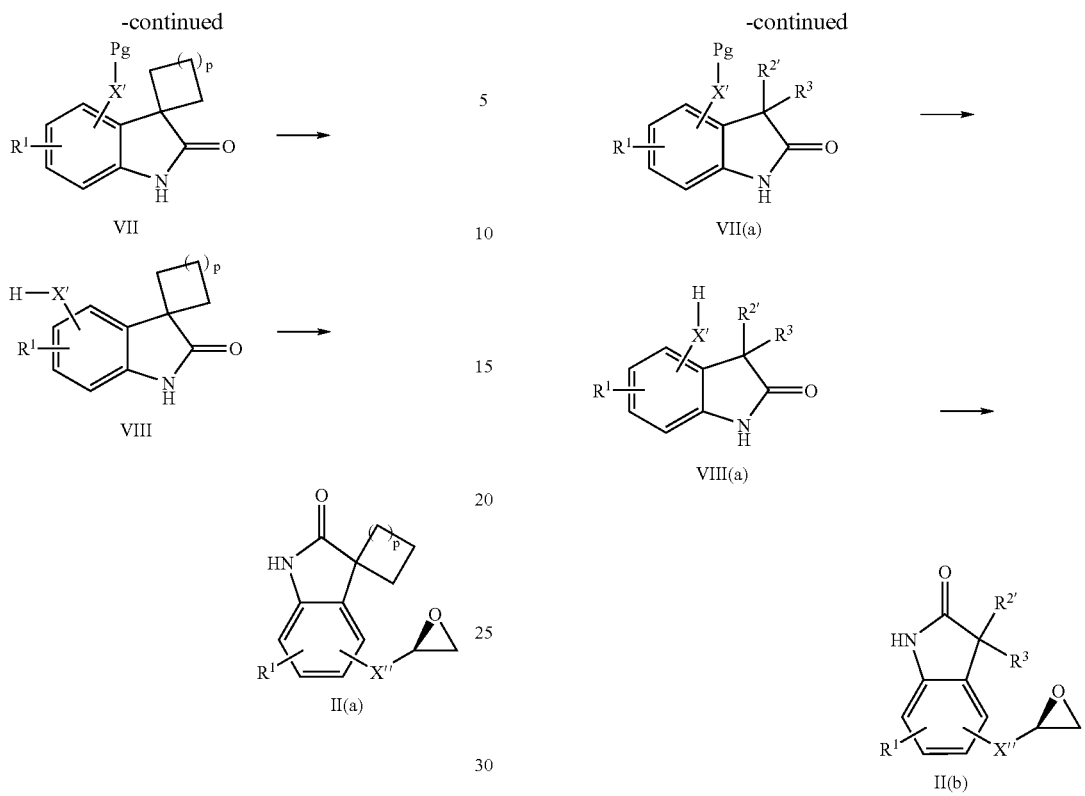

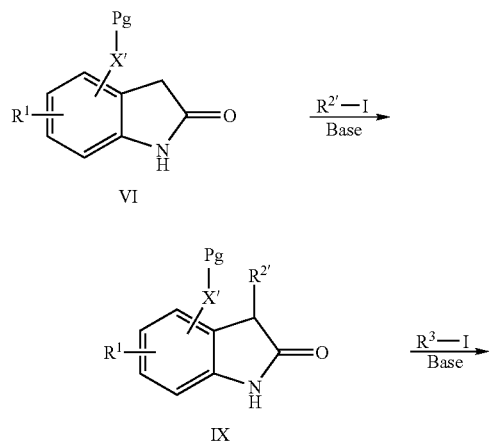

The compounds of formula II(a) and II(b) may be prepared by reacting equimolar amounts of a compound of formula VIII or VIII(a), respectively, with (2S)-(+)-glycidyl 3-nitrobenzenesulfonate. The reaction is typically performed in an inert solvent such as acetone and in the presence of a slight excess of a weak base, such as potassium carbonate. The suspension may then be heated at reflux for 16–20 hours with stirring to provide a compound of formula II(a) or II(b).

The cyclopropyl derivatives are prepared by a slightly modified procedure which involves treating the O- and N-diacetylated oxindole with 1,2 dibromoethane and potassium carbonate in dimethylsulfoxide.

The amino starting materials employed in Scheme 1 (formula III compound) may also be prepared by techniques recognized and appreciated by one skilled in the art. For example, an amine of formula III, where $X^2$ is O, may be prepared according to the procedure detailed in Scheme 4.

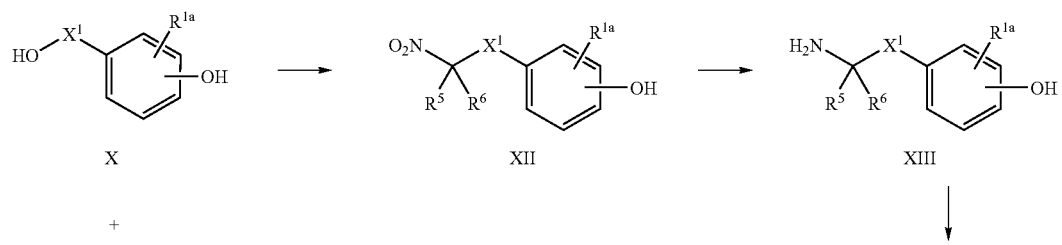

-continued

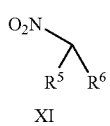

XI

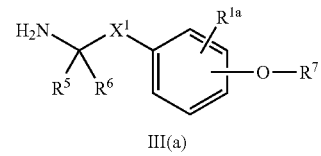

III(a)

A compound of formula XII may be prepared by reacting an arylalkyl alcohol of formula X with excess (5 mol/equivalent) formula X compound by methods well known in the art (see, e.g., *Sh. Prikl. Kin.*, 45:1573–77, 1972). The reaction may also be carried out by mixing the reagents in an aprotic solvent, preferably diglyme, and adding potassium t-butoxide (0.5 mol/equivalent). The reaction is typically heated at reflux until water present in the reaction mixture is removed (generally 2–8 hours). A compound of formula XIII may then be prepared by hydrogenation of the corresponding compound of formula XII over a precious metal catalyst. The hydrogenation can be affected at between 20 and 60 psi of hydrogen (preferably 50 psi), and with a variety of solvents (preferably methanol/acetic acid), temperatures (preferably 50° C.), and catalysts (preferably 5% palladium on carbon wetted with ethanol denatured with toluene) well known in the art.

A skilled artisan will appreciate that a compound of formula XIII could be coupled with a wide variety of aryl halides to yield the claimed ethers. The coupling can be carried out according to procedures well known in the art and is preferably performed by mixing the starting materials in N,N-dimethylacetamide and toluene in the presence of potassium carbonate. The reaction is typically then heated to reflux for 5 to 24 hours to effect the reaction and to remove water present in the reaction mixture.

Compounds of formula $R^{2'}$-I, $R^3$-I, IV, X, XI and

are either commercially available, known in the art, or can be prepared by methods known in the art or described herein.

The following Preparations, Examples and Formulations are provided so that the invention might be more fully understood. They should not be construed as limiting the invention in any way.

PREPARATIONS

Epoxides of Formula II

Epoxides 1–9 are prepared for use as described in Scheme 1. These epoxides are pictured below in Table 1.

TABLE 1

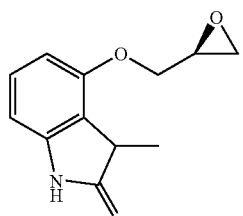

1

TABLE 1-continued

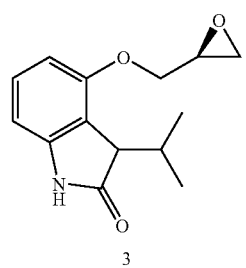

2

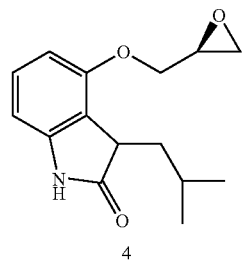

3

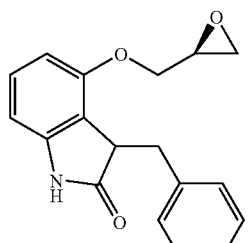

4

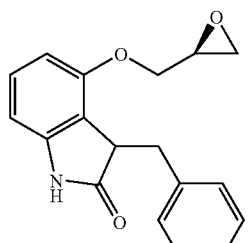

5

TABLE 1-continued

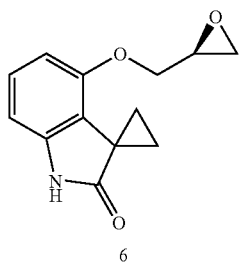
6

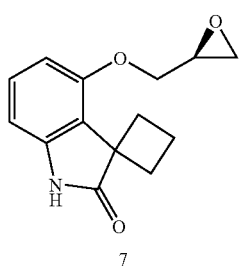
7

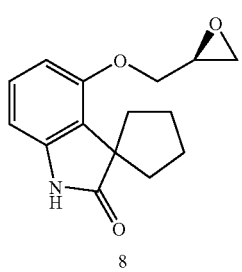
8

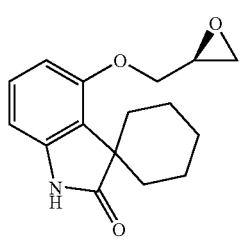
9

Epoxide 1

Hydrazine monohydrate (265 mL, 5.46 mol) is added to a flask containing 4-methoxyisatin (484.26 g, 2.73 mol), sodium acetate (22.31 g, 0.27 mol) and dimethylformamide (2.4 L). The temperature rose from 19.2° C. to 31.9° C. within 5 minutes, and when the exotherm had ceased the solution is further heated to 110° C. over 40 minutes. Vigorous off-gassing is observed, and the temperature rose above the set point slowly. After 30 minutes the temperature stabilized at 110° C. and the gas evolution tapered off. The solution is kept at 110° C. for 40.5 hours at which point the heating mantle is removed and the solution is allowed to cool. At 40° C., the solution is seeded with 100 mg of 4-methoxyindole, and the contents are cooled to 17° C. with an ice bath. The resulting mixture is poured into water (6.2 L) which had been pre-cooled to 6° C. The flask is rinsed with water (600 mL), and the thick slurry is cooled to 4° C. before being filtered through polypropylene. The filter cake is rinsed with water (3×1.5 L) and the solid is dried in a 50° C. vacuum oven to provide 353 g of 4-methoxyindolin-2-one.

A mixture of tetrahydrofuran (990 mL), 4-methoxyindolin-2-one (*J. Chem. Soc.*, 3904, 1952; *Tetrahedron*, 24:6093, 1968, 39.60 g, 242.7 mmol), and N,N,N',N'-tetramethylethylenediamine (56.40 g, 485.4 mmol) is cooled to −78° C. N-butyllithium (379.2 mL, 606.7 mmol, 1.6M in hexanes) is added over 1 hour so as to maintain the reaction temperature between −70° C. and −69° C. After stirring the mixture for 50 minutes at −78° C., iodomethane (36.17 g, 254.8 mmol) is added over 50 minutes at −78° C. to −64° C. The reaction mixture is allowed to warm to −40° C. and iodomethane (48.23 g, 0.3398 mol) is added incrementally over 1 hour until the starting material is less than 3 percent by HPLC (retention 7.3 minutes; Zorbax SB-Phenyl (4.6 mm×25 cm); solvent A—trifluoroacetic acid solution (0.1%, v/v); solvent B—acetonitrile; 1.0 mL/min; 254 nm; gradient method: 0.00–2.00 minutes, 30% A, 70% B; 2.00–7.00 minutes, linear ramp from 30% A, 70% B to 80% A, 20% B; 7.00–15.00 minutes, 80% A, 20% B). Methanol (20 mL) is added to the reaction mixture over 15 minutes at −60° C. to −50° C. Aqueous hydrochloric acid (1N, 250 mL) is added allowing the temperature to rise to −4° C. The solution is transferred to a separatory funnel with ethyl acetate (500 mL), aqueous hydrochloric acid (1N, 250 mL) and a saturated sodium chloride solution (250 mL). After separating, the organic layer is extracted twice with aqueous hydrochloric acid (1N, 250 mL) and the aqueous layer is extracted with ethyl acetate (250 mL). The combined organic layers are washed with a saturated sodium chloride solution (250 mL) then dried over magnesium sulfate. After filtration, the solvents are removed by rotary evaporation to give 43.58 g (91.6%) of 4-methoxy 3-methyl-1,3-dihydro-indol-2-one as a solid, mp 128–130° C. MS (ES+) m/z 178 (M⁺+1).

4-Methoxy-3-methyl-1,3-dihydro-indol-2-one is demethylated according to Representative Procedure 1 below to form 4-hydroxy-3-methyl-1,3-dihydro-indol-2-one. 4-Hydroxy-3-methyl-1,3-dihydro-indol-2-one is coupled to (2S)-glycidyl 3-nitrobenzenesulfonate to form the title epoxide according to Representative Procedure 2 below.

Epoxide 2

A solution of 4-methoxy-3-methyl-1,3-dihydro-indol-2-one (41.73 g, 235.5 mmol) and tetrahydrofuran (1000 mL) is cooled to −78° C. Potassium bis(trimethylsilyl)amide (989.0 mL, 494.3 mmol, 0.5 M in toluene) is added over 45 minutes so as to maintain the reaction temperature between −71° C. and −66° C. Iodomethane (36.71 g, 258.7 mmol) is added over 15 minutes between −75° C. and −70° C. The mixture is stirred at −78° C. for 1 hour then −60° C. for 30 minutes. Methanol (25 mL) is added at −60° C. Aqueous hydrochloric acid (1N, 420 mL) is added rapidly allowing the temperature to rise to −7° C. The solution is transferred to a separatory funnel with aqueous hydrochloric acid (1N, 420 mL) and toluene (50 mL). The organic layer is extracted with a saturated sodium bicarbonate solution (250 mL), washed with a saturated sodium chloride solution (200 mL), dried over magnesium sulfate, and filtered. The filtrate is stirred with DARCO (25 g) for 1 hour then filtered. The filtrate is concentrated by rotary evaporation. The residue is refluxed for 1 hour in tert-butyl methyl ether (300 mL). After distilling out 100 mL of solvent, the slurry is stirred for 10 hours at 24° C. The solid is isolated by vacuum filtration rinsing twice with cold (−40° C.) tert-butyl methyl ether. After vacuum drying for 12 hours at 50° C./5 Torr, 23.9 g (58%) of 4-methoxy-3,3-dimethyl-1,3-dihydro-indol-2-one is obtained. mp 143–144° C. MS (ES+) m/z 192 (M$^+$+1).

Pyridine hydrochloride (51.10 g, 442.2 mmol) and 4-methoxy-3,3-dimethyl-1,3-dihydro-indol-2-one (21.61 g, 113.0 mmol) are combined and stirred in a melt at 220° C. for 45 minutes. Heating is removed and when the mixture cooled to 100° C., water (60 mL) is added, followed by ethyl acetate (150 mL) at 65° C. The layers are separated and the aqueous phase is extracted five times with ethyl acetate (50 mL). The combined organic layers are extracted first with a combination of aqueous hydrochloric acid (1N, 10 mL) and a saturated solution of sodium chloride (10 mL), then with a combination of a saturated solution of sodium bicarbonate (10 mL) and a saturated solution of sodium chloride (10 mL). After drying over magnesium sulfate, the solvent is removed via rotary evaporation. The crude material is dissolved in ethyl acetate (200 mL) and hexane (200 mL) at 60° C. Crystallization is allowed to begin slowly over 1 hour at 50° C. After stirring for 12 hours at 24° C., the slurry is cooled to 0° C. for 1 hour, then vacuum filtered washing twice with cold 1:1, ethyl acetate:hexane (35 mL, 0° C.) to provide 13.8 g (98.6% purity, 68% yield) of 4-hydroxy-3,3-dimethyl-1,3-dihydro-indol-2-one, mp 224–225° C. MS (ES+) m/z 178 (M$^+$+1). From the filtrate a second crop (5.0 g, 98.4% purity, 25% yield) is obtained to give a total yield of 93%.

Acetone (250 mL), 4-hydroxy-3,3-dimethyl-1,3-dihydro-indol-2-one (17.56 g, 99.1 mmol), powdered potassium carbonate (28.70 g, 208.1 mmol) and (2S)-(+)-glycidyl 3-nitrobenzenesulfonate (26.20 g, 101.1 mmol) are combined and the resulting mixture is refluxed for 22.5 hours. The solvent is removed by rotary evaporation and the crude material is purified by flash chromatography (500 g SiO$_2$; 1:1, ethyl acetate:hexane). During solvent removal from the product fractions, hexane (200 mL) is added and the product is crystallized in two crops. Isolation by vacuum filtration followed by vacuum drying at 50° C./5 Torr for 12 hours provided 11.0 g (47%) of the title epoxide, mp 156–158° C. MS (ES+) m/z 234 (M$^+$+1).

Epoxide 3

A mixture of 4-methoxyoxindole (3.0 g, 18.4 mmol) and piperidine (3.5 mL, 36.89 mmol) in acetone (100 mL) is heated at reflux for 18 hours. The mixture is concentrated to dryness and triturated with methanol (20 mL). Filtration removed 800 mg of unreacted 4-methoxyoxindole. The filtrate is preadsorbed on silica gel (5 g), and purified by flash chromtography (120 g SiO$^2$, 25% ethyl acetate:hexane to 50% ethyl acetate:hexane) to provide 700 mg (19%) of 3-isopropylidene-4-methoxy-1,3-dihydro-indol-2-one. MS (ESI+) 204.

A mixture of 3-isopropylidene-4-methoxy-1,3-dihydro-indol-2-one (700 mg, 3.4 mmol) and 5% palladium on carbon (88 mg) in ethanol (25 mL) is hydrogenated at 60 psi overnight. Filtration and removal of the solvent in vacuo provided 560 mg (79%) of 3-isopropyl-4-methoxy-1,3-dihydro-indol-2-one. MS (ESI+) 206.

3-Isopropyl-4-methoxy-1,3-dihydro-indol-2-one is demethylated according to Representative Procedure 1 below in 45% yield. MS (ESI+) 192. 3-Isopropyl-4-hydroxy-1,3-dihydro-indol-2-one is coupled to (2S)-glycidyl 3-nitrobenzenesulfonate to form the title epoxide according to Representative Procedure 2 below.

Epoxide 4

3-Isobutyl-4-methoxy-1,3-dihydro-indol-2-one is prepared from 4-methoxyoxindole (3.1 mmol) and 1-iodo-2-methylpropane (3.1 mmol) substantially as described above for Epoxide 1 and Epoxide 2. The compound is purified by flash chromatography (SiO$_2$, 25% ethyl acetate:hexane) to obtain 180 mg (27%) of the desired compound. MS (ESI+) 220.

3-Isobutyl-4-methoxy-1,3-dihydro-indol-2-one is demethylated according to Representative Procedure 1 below in 80% yield. MS (ESI+) 206. 3-Isobutyl-4-hydroxy-1,3-dihydro-indol-2-one is coupled to (2S)-glycidyl 3-nitrobenzenesulfonate to form the title epoxide according to Representative Procedure 2 below. MS (ESI+) 262.

Epoxide 5

3-Benzyl-4-methoxy-1,3-dihydro-indol-2-one is prepared from 4-methoxyoxindole (4.8 mmol) and benzyl bromide (5.3 mmol) substantially as described above for Epoxide 4. The compound is purified by flash chromatography (SiO$_2$, 25% ethyl acetate:hexane) to obtain the desired compound (36%). MS (ESI+) 254.

3-Benzyl-4-methoxy-1,3-dihydro-indol-2-one is demethylated according to Representative Procedure 1 below in 73% yield. MS (ESI+) 240. 3-Benzyl-4-hydroxy-1,3-dihydro-indol-2-one is coupled to (2S)-glycidyl 3-nitrobenzenesulfonate to form the title epoxide according to Representative Procedure 2 below. MS (ESI+) 296.

Epoxide 6

To a mixture of 4-(acetyloxy)-1,3-dihydro-2H-indol-2-one (J. Med. Chem., 38:2802–2808, 1995; 1.44 g, 7.5 mmol) and sodium carbonate (5.3 g, 50 mmol) in tetrahydrofuran (50 mL) is added acetic anhydride (4.3 mL, 45 mmol). The mixture is stirred at ambient temperature for 18 hours, and partitioned between ethyl acetate and water. After drying (magnesium sulfate), the solvent is removed in vacuo. The crude material is preadsorbed on silica gel (10 g), and purified by flash chromtography (90 g SiO$_2$, 10% ethyl acetate:hexane to 70% ethyl acetate:hexane, linear gradient over 30 minutes) to provide 480 mg (27%) of acetic acid 1-acetyl-2-oxo-2,3-dihydro-1H-indol-4-yl ester as a white solid.

By a procedure substantially similar to that described in Heterocyclic Chem., 31:1513, 1994, a mixture of acetic acid 1-acetyl-2-oxo-2,3-dihydro-1H-indol-4-yl ester (0.48 g, 2.1 mmol) and potassium carbonate (0.57 g, 4.1 mmol) in dimethylsulfoxide (20 mL) is treated with 1,2-dibromoethane (0.39 mL, 4.5 mmol). The mixture is stirred at room temperature for 18 hours, and partitioned between diethylether and water. The aqueous phase is extracted with diethylether (2×), and the combined organic phase is washed with brine, dried (magnesium sulfate), filtered and concentrated to dryness. The crude material is preadsorbed on silica gel (7 g), and purified by flash chromtography (90 g SiO$_2$, 10% ethyl acetate:hexane to 70% ethyl acetate:hexane, linear gradient over 40 minutes) to yield 420 mg (79%) of 3-spirocyclopropane-4-methoxy-1,3-dihydro-indol-2-one. MS (ESI+) 260.

A mixture of 3-spirocyclopropane-4-methoxy-1,3-dihydro-indol-2-one (0.42 g, 1.6 mmol) in aqueous sulfuric acid (3N, 15 mL) and tetrahydrofuran (15 mL) is heated at reflux for 2 hours. The mixture is partitioned between ethyl acetate and water. The aqueous phase is extracted twice with ethyl acetate, and the combined organic phase is washed with brine, and dried (magnesium sulfate). After removal of the solvent under reduced pressure, the crude material is preadsorbed on silica gel (5 g), and purified by flash chromtography (40 g SiO$_2$, 10% ethyl acetate:hexane to 70% ethyl acetate:hexane, linear gradient over 40 minutes) to yield 140 mg (50%) of 3-spirocyclopropane-4-hydroxy-1,3-dihydro-indol-2-one. MS (ESI+) 176.

3-Spirocyclopropane-4-hydroxy-1,3-dihydro-indol-2-one is coupled to (2S)-glycidyl 3-nitrobenzenesulfonate to form the title epoxide according to Representative Procedure 2 below. MS (ESI+) 232.

Epoxide 7

A suspension of 4-methoxy-1,3-dihydro-indol-2-one (3.7 g, 22.9 mmol) in tetrahydrofuran (110 mL) is cooled to –78° C. using a dry ice/acetone bath and treated with N,N,N',N'-tetramethylethylenediamine (8.6 mL, 57.1 mmol). N-butyllithium (36.0 mL, 57.1 mmol, 1.6 M in hexanes) is added dropwise, and the mixture stirred at this temperature for 30 minutes. 1,3 Diiodopropane (13.2 mL, 114.5 mmol) is added and the mixture is slowly warmed to room temperature and stirred for 18 hours. The reaction is quenched by addition of methanol (50 mL), followed by 1N aqueous hydrochloric acid to dissolve the resulting solids. The resulting mixture is partitioned between ethyl acetate and brine. The aqueous phase is then extracted twice with ethyl acetate, and the combined organic phases are washed with brine, dried (magnesium sulfate), and concentrated. The crude material is preadsorbed on silica gel (15 g) and purified by flash chromatography (90 g silica gel, 15% ethyl acetate/hexane to 50% ethyl acetate/hexane with a linear gradient over 45 minutes to afford 1.55 g of 3-spirocyclobutane-4-methoxy-1,3-dihydro-indol-2-one (33%). MS (ESI+) 204.

To a solution of 3-spirocyclobutane-4-methoxy-1,3-dihydro-indol-2-one (1.55 g, 7.6 mmol) in dichloromethane (100 mL) at –78° C. is added dropwise a solution of boron tribromide in dichloromethane (1M, 38 mL, 38 mmol). After the mixture is stirred at –78° C. for 1 hour, the cooling bath is removed, and the mixture is allowed to warm to room temperature and stir overnight. The reaction is quenched by the addition of ice and water. The mixture is extracted three times with ethyl acetate, and the combined organic phases are dried (magnesium sulfate), and concentrated. The crude material is preadsorbed on silica gel (7 g), and purified by flash chromatography (40 g silica gel, 25% ethyl acetate:hexane to 60% ethyl acetate:hexane, linear gradient over 45 minutes) to yield 750 mg (52%) of 3-spirocyclobutane-4-hydroxy-1,3-dihydro-indol-2-one. MS (ESI+) 190.

3-Spirocyclobutane-4-hydroxy-1,3-dihydro-indol-2-one is coupled to (2S)-glycidyl 3-nitrobenzenesulfonate to form the title epoxide according to Representative Procedure 2 below. MS (ESI+) 246.

Epoxide 8

To a mixture of tetrahydrofuran (1000 mL) and 4-methoxy-1,3-dihydro-indol-2-one (48.30 g, 296.0 mmol) cooled to –65° C. wad added N,N,N',N'-tetramethylethylenediamine (89.02 g, 766.0 mmol) maintaining the temperature between –65° C. and –63° C. After cooling further to –75° C., N-butyllithium (478.8 mL, 766.0 mmol, 1.6 M in hexanes) is added over 1 hour so as to maintain the temperature between –75° C. and –73° C. After stirring the mixture for 30 minutes at –72° C., 1,4-dibromobutane (330.82 g, 1.5321 mol) is added over 1 hour between –72° C. and –62° C. The solution is stirred at –33° C. for 15 hours then at 24° C. to 30° C. for 5 hours. Methanol (63 mL) is added to the mixture and the pH is adjusted to 6 with concentrated hydrochloric acid (50 mL), 3N aqueous hydrochloric acid (50 mL) and 1N aqueous hydrochloric acid (500 mL). Ethyl acetate (1000 mL) and a saturated solution of sodium chloride (300 mL) are added. The organic layer is separated and extracted with a combination of a saturated solution of sodium bicarbonate (500 mL) plus a saturated solution of sodium chloride (300 mL) then dried over magnesium sulfate. After filtration the solvent is removed by rotary evaporation at 44° C./5 Torr until no further distillate is obtained. Heptane (500 mL) is added and removed twice by rotary evaporation. Heptane (250 mL) is added and the mixture is stirred at 24° C. after which the solid is collected by vacuum filtration and rinsed three times with heptane (100 mL). After vacuum drying at 60° C./5 Torr for 14 hours, 53.1 g (94.3% purity, 78% yield) of 3-spirocyclopentane-4-methoxy-1,3-dihydro-indol-2-one is obtained as a solid, mp 168–169° C. MS (ES+) m/z 218 (M$^+$+1). From the filtrate a second crop (3.6 g, 96.3% purity, 6% yield) is obtained to give a total yield of 84%.

Alternatively, 3-spirocyclopentane-4-methoxy-1,3 dihydro-indol-2-one can be prepared as follows. A slurry of 4-methoxyindolin-2-one (200 g, 1.2 mol) and tetrahydrofuran (2.6 L) is cooled to –70° C. in a dry ice/acetone bath. A solution of sodium bis(trimethylsilyl)amide and tetrahydrofuran (4.9 L, 1M soln) pre-cooled to 4° C. is added to this slurry over 1.5 hours while maintaining a temperature of $\leq$–69° C. The resulting solution is maintained at this temp for 20 minutes post addition at which point 1,4 dichlorobutane (347 g, 2.7 mol) is added in one portion. The cooling bath is removed and the solution is allowed to warm to 30° C. over 4.5 hours. The solution is then heated to 35° C. for an additional 15.5 hours. Quenching is effected with methanol (260 mL) followed by water (3 L), and lastly, after installation of an ice bath, concentrated hydrochloric acid (640 mL) until the pH of the mixture is 2. The layers are separated and the aqueous layer is rinsed with ethyl acetate (1.6 L), and the combined organic layers are washed with 1N aqueous hydrochloric acic/saturated sodium chloride (1.8 L/1.0 L). Again the aqueous layer is back-extracted with ethyl acetate (1.2 L). The combined organic layers are rinsed with saturated sodium bicarbonate/saturated sodium chloride (1.2 L/1.2 L), dried (magnesium sulfate, 170 g) and filtered. The filtrate is then transferred to a rotary evaporator where a solvent exchange with heptane (4 L) is performed. When the slurry volume approaches 2 L it is cooled, filtered and dried in a 50° C. vacuum oven overnight to provide a granular orange solid (241.3, 91%) which is used without further purification.

Pyridine hydrochloride (127.6 g, 1.1042 mol) and 3-spirocyclopentane-4-methoxy-1,3-dihydro-indol-2-one (48.29 g, 0.2223 mol) are combined and stirred in a melt at 220° C. for 80 minutes. Heating is removed and at 100° C., water (150 mL) is added followed by ethyl acetate (300 mL) at 60° C. The layers are separated and the aqueous phase is extracted four times with ethyl acetate (100 mL). The combined organic layers are extracted first with a combination of aqueous hydrochloric acid (1N, 100 mL) and a saturated solution of sodium chloride (100 mL), then with a combination of a saturated solution of sodium bicarbonate (100 mL), a saturated solution of sodium chloride (100 mL), and water (200 mL). After drying over magnesium sulfate, the solvent is removed by rotary evaporation. The crude material is purified by flash chromatography (5 kg silica gel; 5.4% methanol, 43.3% heptane, 51.3% methylene chloride)

to provide 38.7 g (85%) of 3-spirocyclopentane-4-hydroxy-1,3-dihydro-indol-2-one as a solid, mp 215–216° C. MS (ES+) m/z 204 (M$^+$+1).

Acetone (750 mL), 3-spirocyclopentane-4-hydroxy-1,3-dihydro-indol-2-one (37.76 g, 0.1858 mol), powdered potassium carbonate (53.92 g, 0.3901 mol) and (2S)-(+)-glycidyl 3-nitrobenzenesulfonate (50.57 g, 0.1951 mol) are combined and the resulting yellow mixture refluxed for 20 hours. After the solvent is removed by rotary evaporation, the resulting solid is dissolved in ethyl acetate (750 mL), water (2500 mL), and a saturated solution of sodium chloride (100 mL). The aqueous layer is separated and extracted with ethyl acetate (250 mL). The combined organic layers are extracted with a saturated solution of sodium chloride (200 mL), dried over sodium sulfate, and concentrated by rotary evaporation. The crude material is purified by flash chromatography (5 kg silica gel; 12 L of 3.0% methanol, 55.0% heptane, 42.0% methylene chloride; then 9 L of 5.0% methanol, 47.5% heptane, 47.5% methylene chloride). After vacuum drying at 50° C./5 Torr for 12 hours, 39.0 g (81%) of the title epoxide is obtained as a solid, mp 153–154° C. MS (ES+) m/z 260 (M$^+$+1).

Epoxide 9

A suspension of 4-methoxy-1,3-dihydro-indol-2-one (2.0 g, 212.3 mmol) in tetrahydrofuran (60 mL) is cooled to −78° C. using a dry ice/acetone bath and treated with N,N,N',N'-tetramethylethylenediamine (3.7 mL, 24.6 mmol). N-butyllithium (15.4 mL, 24.6 mmol, 1.6 M in hexanes) is added dropwise, and the mixture stirred at this temperature for 30 minutes. The mixture is warmed to −20° C., and 1,5-diiodopentane (9.2 mL, 61.5 mmol) is added, the mixture slowly warmed to room temperature and stirred for 18 hours. The reaction is quenched by addition of a saturated aqueous ammonium chloride solution and partitioned between ethyl acetate and 1N aqueous hydrochloric acid. The aqueous phase is then extracted twice with ethyl acetate, and the combined organic phases are washed with brine and dried (magnesium sulfate). After removal of the solvent, the crude material is purified by flash chromatography (90 g silica gel, hexane to 50% ethyl acetate:hexane) to yield 1.13 g (40%) of 3-spirocyclohexane-4-methoxy-1,3-dihydro-indol-2-one. MS (ESI+) 232.

3-Spirocyclohexane-4-methoxy-1,3-dihydro-indol-2-one is demethylated according to Representative Procedure 1 below in 32% yield. MS (ESI+) 218. 3-Spirocyclohexane-4-hydroxy-1,3-dihydro-indol-2-one is coupled to (2S)-glycidyl 3-nitrobenzenesulfonate to form the title epoxide according to Representative Procedure 2 below.

Representative Procedure 1: Demethylation

An intimate mixture of the 4-methoxyindole and pyridine hydrochloride (approximately 10 g per gram oxindole) is heated for 15–45 minutes at 210–220° C. in an oil bath. The reaction is cooled to room temperature, and the solid is added to a mixture of ice and ammonium hydroxide solution. This water mixture is evaporated, and the crude material preabsorbed on silica gel. A flash column in 25–50% ethyl acetate/hexanes provided the desired phenols in yields of 32–94%

Representative Procedure 2: Epoxide Formation

A mixture of the 4-hydroxyoxindole (1 equivalent), (2S)-glycidyl 3-nitrobenzenesulfonate (1.2 equivalents), potassium carbonate (1.2 equivalents) and acetone (resulting solution 0.2M in oxindole) is refluxed for 16 hours, cooled to room temperature and the solids removed via filtration. The filtrate is concentrated, redissolved in ethyl acetate and extracted several times with water; The organic layer is concentrated and the crude product could be purified by flash chromatography (25% ethyl acetate/hexanes) to give the desired epoxides. However, in most cases the epoxide is used in the subsequent reactions without further purification.

Amines of Formula III

Amines 1–38 are prepared for use as described in Scheme 1. These amines are pictured below in Table 2.

TABLE 2

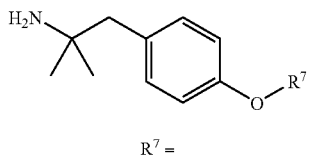

R$^7$ =

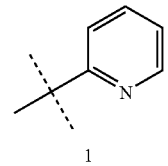

1

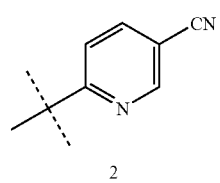

2

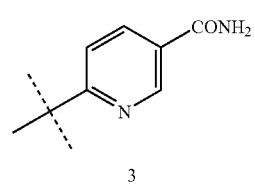

3

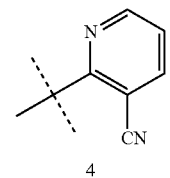

4

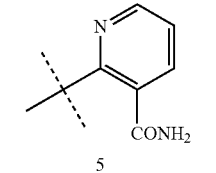

5

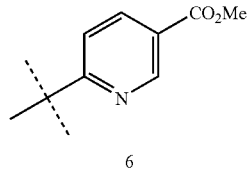

6

TABLE 2-continued
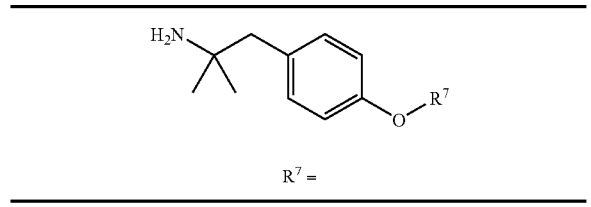
R⁷ =
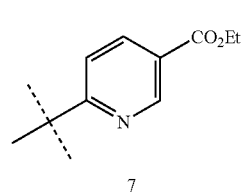
7
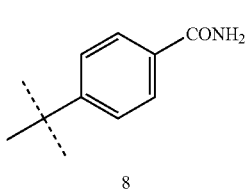
8
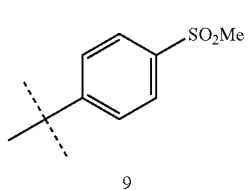
9
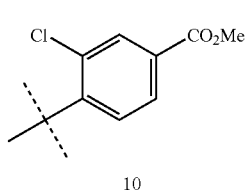
10
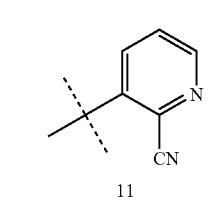
11
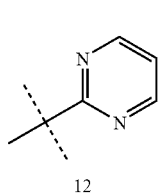
12
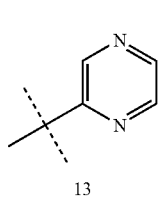
13
TABLE 2-continued
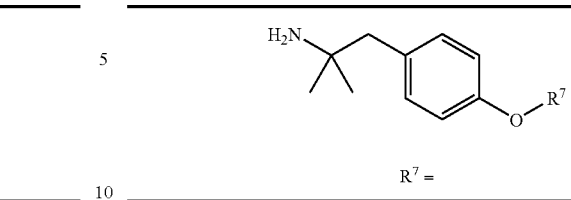
R⁷ =
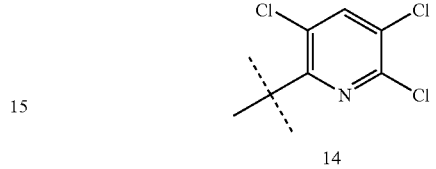
14
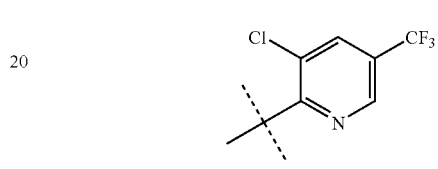
15
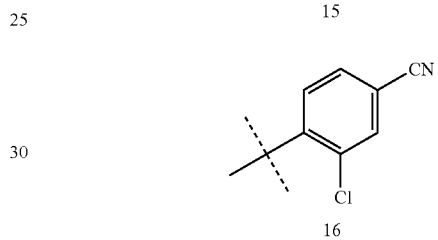
16
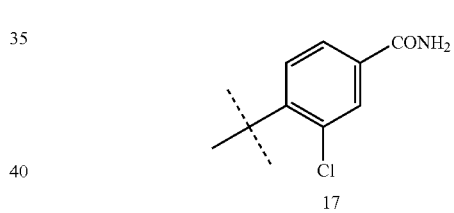
17
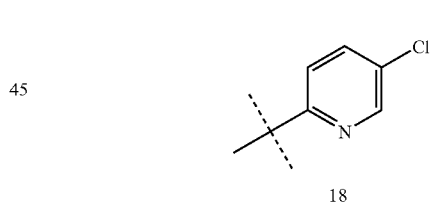
18
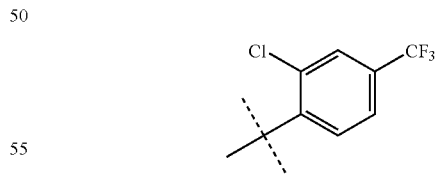
19
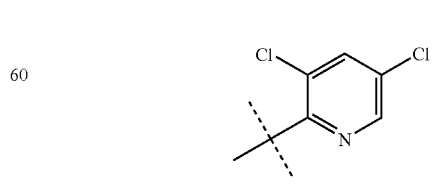
20

TABLE 2-continued
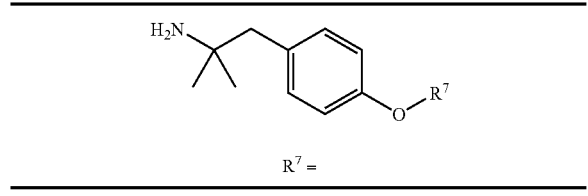
R⁷ =
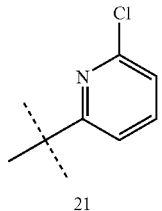
21
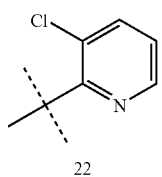
22
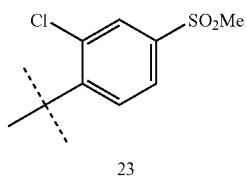
23
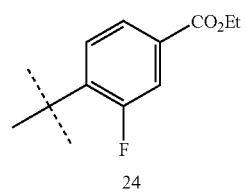
24
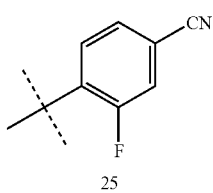
25
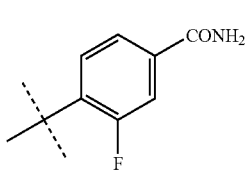
26
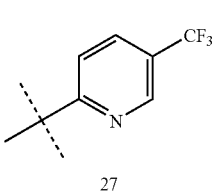
27
TABLE 2-continued
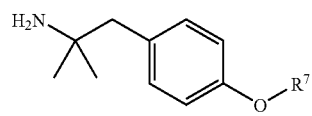
R⁷ =
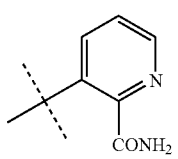
28
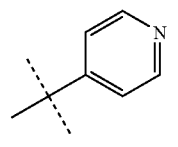
29
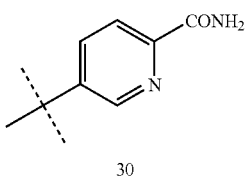
30
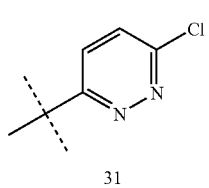
31
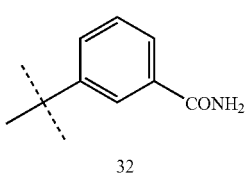
32
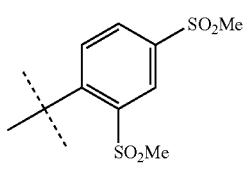
33
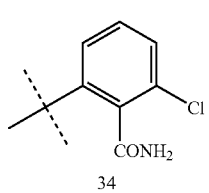
34

TABLE 2-continued

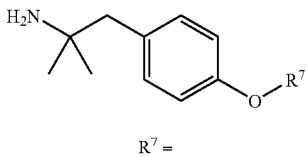

R[7] =

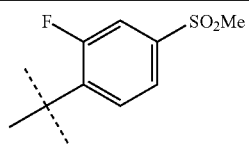

35

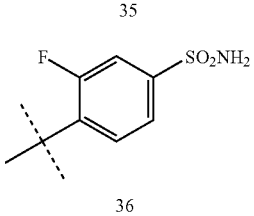

36

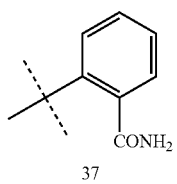

37

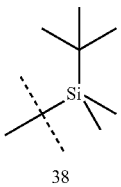

38

Amines 1 and 9 may be prepared according to procedures detailed in U.S. Ser. No. 09/068,192, the teachings of which are herein incorporated by reference. Amines 10 and 25 may be prepared by a procedure substantially similar to that described for Amine 1. Amines 2, 3 and 8 may be prepared according to procedures detailed in U.S. Pat. No. 5,977,154, the teachings of which are herein incorporated by reference. Amines 26, 28 and 37 may be prepared by a procedure substantially similar to that described for Amine 8. Amine 32 may be prepared by a procedure substantially analogous to Amine 3. Amine 38 may be prepared according to procedures detailed in U.S. Pat. No. 5,840,738, the teachings of which are herein incorporated by reference.

Amine 4

4-(2-Amino-2-methylpropyl)phenol (50.8 g, 225 mmol), 2-chloro-3-cyanopyridine (30.8 g, 222 mmol), potassium carbonate (77.7 g, 562 mmol, powdered), N,N-dimethylacetamide (609 ml), and isooctane (122 ml) are combined and heated to reflux. The water formed during the reaction is removed azeotropically via a Dean-Stark trap. After about 1–2 hours the reaction is complete. The slurry is cooled to 30° C. and filtered. The filter cake is washed with N,N-dimethylacetamide (250 ml) and the combined organic fractions are concentrated by rotary evaporation at 80° C. The resulting dark green oil is dissolved in dichloromethane (580 ml), and washed with water (160 ml). The phases are separated and the organic phase washed with water (250 ml). Water (1 L) is added to the organic phase and the pH adjusted to 1 with 12N aqueous hydrochloric acid (about 25 ml). The phases are separated and the acidic aqueous layer is washed with dichloromethane (250 ml). Dichloromethane (1 L) is added to the acidic aqueous phase and the pH is adjusted to 12–13 with 5N aqueous sodium hydroxide. The phases are separated and the organic phase is dried over sodium sulfate. After filtration the solution is concentrated to give 53 g of the title amine (88%).

Amine 6

4-(2-Amino-2-methylpropyl)phenol (3.00 g, 18.2 mmol), methyl 6-chloronicotinate (3.27 g, 19.1 mmol), powdered potassium carbonate (3.76 g, 27.2 mmol, 300 mesh), N,N-dimethylacetamide (60 ml), and toluene (15 ml) are combined and heated to reflux. The water formed during the reaction is removed azeotropically via a Dean-Stark trap. After about 2 hours, the internal temperature reached 154° C. and the reaction is complete. The slurry is cooled to 30° C. and filtered. The filter cake is washed with N,N-dimethylacetamide and the combined organic fractions concentrated by rotary evaporation at 75° C. The resulting oil is dissolved in ethyl acetate (50 ml), and washed with water (30 ml). The phases are separated and the aqueous phase is extracted with ethyl acetate (20 ml) after some saturated aqueous sodium chloride solution (10 ml) is added to facilitate phase separation. The combined organic fractions are washed with water (2×30 ml) and saturated aqueous sodium chloride (30 ml) and then dried over sodium sulfate. After filtration the solution is concentrated to give 4.60 g (80%) of the title amine.

Amine 7

4-(2-Amino-2-methylpropyl)phenol acetic acid salt (45.1 g, 0.200 mol), powdered potassium carbonate (58.1 g, 0.420 mol, 300 mesh), and isooctane (140 mL) are added sequentially to N,N-dimethylacetamide (500 mL) and the resulting mixture is heated to reflux under a Dean-Stark trap until water production -almost ceased (about 2 hours, 121° C. internal temperature). A solution of ethyl 6-chloronicotinate (39.0 g, 0.210 mol) in N,N-dimethylacetamide (50 mL) is added over 15 minutes and the reaction heated at reflux, continuing to remove any water or alcohol as formed, until the reaction is complete by HPLC (about 2 hours). The slurry is cooled to room temperature and filtered through a one quarter inch pad of celite and the cake is rinsed with methyl tert-butyl ether (2×75 mL). The filtrate is then concentrated by rotary evaporation to a net weight of about 134 g. The resulting oil is dissolved in methyl tert-butyl ether (315 mL) and washed with water (315 mL). The product is extracted from the organic phase with aqueous hydrochloric acid (1N, 220 mL) and water (140 mL). Ethyl acetate (315 mL) is added to the aqueous phase and the mixture basified with a solution of sodium carbonate (1.2 equivalents in 135 mL water) with stirring. Caution: foaming may occur. The phases are separated and the organic phase is washed with 10% w/w aqueous solution of sodium chloride (135 mL). The solvent is removed by rotary evaporation, the oil is dissolved in methanol (135 mL), and the solvent concentrated again. The resulting solid is dried overnight at room temperature to afford 61.0 g of the title amine (94% yield) which is used without further purification.

Amine 11

2-Cyano-3-chloropyridine (Bremner, et al., *Syn. Comm.*, 27:1535, 1997; Kaneda, et al., *Chem. Pharm. Bull.*, 33:565, 1985) is coupled to 4-(2-amino-2-methylpropyl)phenol to prepare the title amine by a procedure substantially similar to that described above for Amine 4.

Amine 23

Potassium tert-butoxide (58.6 ml, 58.6 mmol, 1M in tetrahydrofuran) is added to a solution of 3,4-dichlorothiophenol (10.0 g, 55.8 mmol) in tetrahydrofuran (300 ml) at 0° C. and the solution stirred for 30 minutes. Methyl iodide (8.32 g, 58.6 mmol) is added dropwise and the resulting slurry is stirred for 16 hours. The solvents are removed in vacuo and the residue is dissolved in 150 ml each of methyl-t-butyl ether and 1M $NaHSO_4$. The phases are separated and the organic layer is washed with 150 ml each of water and saturated aqueous sodium chloride. The organic layer is dried over sodium sulfate, filtered and concentrated in vacuo to give 9.67 g of 3,4-dichlorophenyl methylsulfide (90%).

The sulfide from above is converted to the corresponding sulfone as described below for Amine 37. The 3,4 dichloromethyl sulfone is coupled to 4-(2-amino-2-methylpropyl) phenol to prepare the title amine by a procedure substantially similar to that described above for Amine 4.

Amine 30

To a 1 gallon autoclave is added 2,5-dichloropyridine (123 g, 830 mmol), palladium II acetate (5.6 g, 24.9 mmol), 1,3-bis(diphenylphosphine)propane (20.5 g, 49.8 mmol), 1,1,1,3,3,3,-hexamethyldisilazane (700 ml), acetonitrile (1180 ml) and dimethylformamide (295 ml). The autoclave is pressurized to 70 psi with carbon monoxide and heated to 80° C. for 16 hours. The reaction mixture is filtered and washed with acetonitrile. The mixture is concentrated in vacuo to 590 g and 1 L of water is added. The resulting slurry is cooled to 0° C. and filtered to give 102.6 g (79%) of 2-carboxamido-5-chloropyridine which is used without further purification.

2-Carboxamido-5-chloropyridine is coupled to 4-(2-amino-2-methylpropyl)phenol to prepare the title amine by a procedure substantially similar to that described above for Amine 4.

Amine 33

4-Chloro-1,3-benzenedithiol (3.06 g, 17.3 mmol) is added to a stirred mixture of potassium carbonate (5.20 g, 37.7 mmol) in 10 ml of anhydrous dimethylformamide at room temperature under a nitrogen atmosphere. After five minutes, iodomethane (7.20 g, 50.7 mmol) is added in a dropwise fashion to give an exothermic reaction. The reaction mixture is stirred at room temperature over night. The mixture is then diluted with 50 ml deionized water and extracted with hexanes (3×30 ml). The combined hexane extracts are washed with brine and dried over anhydrous magnesium sulfate. Filtration and evaporation of the solvent gave an oil. This oil is dissolved in 50 ml of glacial acetic acid with stirring and chilled to 0° C. in an ice/water bath. Hydrogen peroxide (30%, 8 ml) is added slowly and the mixture stirred at 0° C. for 15 minutes. The ice bath is removed and the mixture allowed to warm to room temperature for one hour. It is then heated under reflux over night. The reaction mixture is concentrated until a precipitate formed. The mixture is then diluted with 50 ml methylene chloride and 50 ml water, neutralized with saturated sodium bicarbonate solution, and the organic layer collected. The aqueous layer is again extracted with methylene chloride (2×50 ml) and the combined organic layers washed with brine and dried over anhydrous magnesium sulfate. After filtration and concentration, 4.29 g of methyl(4-chloro-3-methylsulfonylphenyl)sulfone is obtained (92%). Methyl(4-chloro-3-methylsulfonylphenyl)sulfone is converted to the title amine by a procedure substantially analogous to that described for Amine 9.

Amine 35

To a solution of n-butyl lithium (0.544 mol) in tetrahydrofuran (700 ml) at −78° C. is added a solution of 3,4-difluorobromobenzene (100 g, 0.518 mol) in 200 ml of tetrahydrofuran. After 10 minutes, a solution of dimethyl disulfide in 100 ml of tetrahydrofuran is added and the resulting reaction mixture is warmed to ambient temperature over 60 minutes. The reaction is concentrated in vacuo and the resulting oil is partitioned between 750 ml methyl-t-butyl ether and 300 ml water. The phases are separated and the organic layer is washed with 300 ml of saturated aqueous sodium chloride, dried over magnesium sulfate, filtered, and concentrated in vacuo. The resulting oil is purified by vacuum distillation to provide 43.08 g of 3,4-difluorophenyl methylsulfide.

Metachloroperbenzoic acid (60.4 mmol) is added portionwise to a solution of the sulfide (43 g, 26.8 mmol) in 1 L of dichloromethane at 0° C. After 15 minutes, the reaction mixture is warmed to ambient temperature and stirred for 1.25 hours. The solids are removed by filtration and the resulting solution washed with 750 ml of 1M sodium bisulfite, 2 L sodium bicarbonate, 1 L water, and 750 ml saturated aqueous sodium chloride. The organic layer is dried over magnesium sulfate, filtered and concentrated in vacuo to give 45.17 g (88%) of 2,4-difluorophenyl methyl sulfone. The sulfone is converted to the title amine by a procedure substantially analogous to that described for Amine 9.

Amines 5, 12–22, 24, 27, 29, 31, 34 and 36

Amines 5, 12–22, 24, 27, 29, 31, 34 and 36 are prepared by procedures substantially similar to that described for Amine 4.

EXAMPLES

Representative Procedure 3: Amination of Epoxide

A vial is charged with a solution of single amine of formula III (0.2M in ethanol or t-butanol, 90 micromolar) and a solution of a single epoxide of formula II (0.2M in dimethylsulfoxide, 80 micromolar). The vial is sealed and heated to 80° C. for 24–48 hours. The solution is cooled to room temperature, diluted with methanol, and passed over a cation exchange column, eluting the basic material with 1N methanolic ammonia.

Representative Procedure 4: Amination of Epoxide

A stirred mixture of an epoxide of formula II (1 equivalent) and an amine of formula III (1–2 equivalents) in ethanol, methanol, n-butanol or t-butanol is heated at 70–80°

C. for 2–72 hours. The solvent is evaporated to dryness to give a crude oil that is optionally diluted with methanol or ethanol and passed over a cation exchange column (eluting the free base product with 1N methanolic ammonia) before further purification.

The final products prepared via Representative Procedure 3 or 4 may be further purified by flash or radial chromatography. Typical chromatography conditions include:

a) using a variable mixture of 25:5:1 chloroform/methanol/ammonium hydroxide and 9:1 chloroform/methanol; b) a variable mixture of 90:10:1 $CH_2Cl_2$/ethanolic $NH_3$ gradient; c) dichloromethane/6–12% methanol, 0.15–0.35M ammonia in dichloromethane gradient; d) methylene chloride with a step gradient to 2–8% methanol; e) chloroform/2.0M ammonia in methanol, from 0–10% to 6–20% gradient elution or f) isocratic 6–8% 2M ammonia in methanol: 92–94% dichloromethane.

Alternatively, the final products may be purified on C18 bonded silica gel using either mass guided or UV guided reverse phase liquid chromatography (acetonitrile/water with 0.01% hydrochloric acid or 0.1% trifluoroacetic acid). When purification of a compound of the present invention results in production of a free base, the free base thus prepared may be salified, e.g., by dissolution of the free base in $CH_2Cl_2$ or diethylether, adding 1M ethanolic HCl or a solution of HCl in diethylether, and evaporating the volatiles, or as described in more detail below.

For example, a hydrochloride salt may be prepared by dissolving the free base in dichloromethane, diethylether, or a mixture of ethyl acetate and methanol and adding 1M ethanolic HCl, a solution of HCl in diethylether, or 0.5M ammonium chloride. The resulting mixture is allowed to stir for a short time, e.g., for five minutes, before evaporating the volatiles and optionally triturating in diethyl ether to give the hydrochloride salt.

The oxalate salts may be prepared by dissolving the free base in a small amount of ethyl acetate, optionally adding methanol for solubility. The resulting solution is treated with 1 equivalent of a 0.5M solution of oxalic acid in ethyl acetate. The reaction mixture is either concentrated in vacuo or centrifuged, separated, and the solids are dried, to give the oxalate salt.

To prepare a succinate salt, the free base may be dissolved in a small amount of ethyl acetate or methanol and then treated with 1 equivalent of succinic acid in methanol. The resulting slurry is dissolved in the minimum amount of methanol then concentrated in vacuo to give the succinate salt.

For products synthesized from Amine 38, after amination of the epoxide, the crude ethanolamine product is further treated with 1M tetrabutyl ammonium fluoride (to remove the t-butyldimethylsilyl protecting group) in tetrahydrofuran and stirred at room temperature in tetrahydrofuran overnight. The product is then isolated as described above.

The table below sets out representative combinations of Amines and Epoxides that are reacted as described above in Representative Procedure 3 or 4. Preparation of desired product is confirmed via mass spectral analysis (MSA). Emax±Standard Error Mean (SEM) data, discussed in the "Demonstration of Function" section below, is also included for said compounds where available. The Emax values represent the average of at least 3 runs except as otherwise indicated.

TABLE 3

| E.g. | Epoxide | Amine | MSA | Isolated Form | Emax (%) ± SEM |
|---|---|---|---|---|---|
| 1 | 1 | 8 | 504.9 | Free Base | 72.6 ± 5.4 |
| 2 | 2 | 1 | 476.3 | Trifluoroacetate | 58.3 ± 5.7 |
| 3 | 2 | 1 | 476.3 | Hydrochloride | Not Tested |
| 4 | 2 | 1 | 476.3 | Free Base | Not Tested |
| 5 | 2 | 2 | 501.3 | Hydrochloride | 61.0 ± 4.5 |
| 6 | 2 | 3 | 519.0 | Free Base | 67.9 ± 2.0 |
| 7 | 2 | 4 | 501.3 | Hydrochloride | 64.0 ± 3.6 |
| 8 | 2 | 5 | 519.3 | Hydrochloride | 67.9 ± 1.4 |
| 9 | 2 | 7 | 548.3 | Trifluoroacetate | Not Tested |
| 10 | 2 | 8 | 518.3 | Trifluoroacetate | 68.3 ± 2.3 |
| 11 | 2 | 9 | 553.3 | Hydrochloride | 59.3 ± 2.6 |
| 12 | 2 | 15 | 578.2 | Trifluoroacetate | 60.6 ± 8.6 |
| 13 | 2 | 16 | 534.2 | Trifluoroacetate | 51.7 ± 4.3 |
| 14 | 2 | 17 | 552.3 | Trifluoroacetate | 57.2 ± 3.1 |
| 15 | 2 | 18 | 510.3 | Trifluoroacetate | 65.1 ± 2.6 |
| 16 | 2 | 19 | 577.3 | Trifluoroacetate | 47.4 ± 2.7 |
| 17 | 2 | 20 | 544.2 | Trifluoroacetate | 52.7 ± 4.5 |
| 18 | 2 | 21 | 510.2 | Trifluoroacetate | 56.2 ± 1.8 |
| 19 | 2 | 22 | 510.2 | Trifluoroacetate | 61.7 ± 1.2 |
| 20 | 2 | 28 | 519.3 | Trifluoroacetate | 69.8 ± 5.4 |
| 21 | 2 | 30 | 519.2 | Trifluoroacetate | 67.1 ± 4.5 |
| 22 | 2 | 31 | 511.2 | Trifluoroacetate | 72.0 ± 1.6 |
| 23 | 2 | 32 | 518.2 | Free Base | 80.4 ± 7.0 |
| 24 | 2 | 34 | 553.2 | Free Base | 66.8 ± 6.4 |
| 25 | 2 | 35 | 571.2 | Trifluoroacetate | 54.5 ± 4.9 |
| 26 | 2 | 36 | 572.2 | Trifluoroacetate | 55.3 ± 5.2 |
| 27 | 3 | 3 | 553.3 | Hydrochloride | 41.7 ± 8.4 |
| 28 | 3 | 5 | 533.4 | Hydrochloride | 49.7 ± 5.1 |
| 29 | 4 | 3 | 547.3 | Hydrochloride | 49.4 ± 5.7 |
| 30 | 5 | 3 | 581.3 | Hydrochloride | 15.7 ± 0.6 |
| 31 | 6 | 3 | 517.3 | Hydrochloride | 76.8 ± 3.3 |
| 32 | 6 | 5 | 517.2 | Hydrochloride | 73.9 ± 1.3 |
| 33 | 7 | 3 | 531.2 | Free Base | 71.2 ± 3.9 |
| 34 | 8 | 1 | 502.3 | Trifluoroacetate | 56.3 ± 4.6 |
| 35 | 8 | 2 | 527.3 | Free Base | 54.6 ± 4.7 |
| 36 | 8 | 2 | 527.3 | Hydrochloride | 49.9 ± 1.7 |
| 37 | 8 | 3 | 545.3 | Free Base | 39.3 ± n = 1 |
| 38 | 8 | 3 | 545.3 | Hydrochloride | 66.3 ± 2.9 |
| 39 | 8 | 4 | 527.3 | Free Base | 67.6 ± 3.1 |
| 40 | 8 | 4 | 527.3 | Hydrochloride | 70.6 ± 4.5 |
| 41 | 8 | 5 | 545.4 | Free Base | Not Tested |
| 42 | 8 | 5 | 545.3 | Hydrochloride | 67.3 ± 9.4 |
| 43 | 8 | 6 | 560.4 | Free Base | 63.6 ± 4.0 |
| 44 | 8 | 7 | 574.1 | Free Base | 64.3 ± 4.1 |
| 45 | 8 | 9 | 579.3 | Free Base | 59.1 ± 4.4 |
| 46 | 8 | 9 | 579.2 | Hydrochloride | 48.8 ± 4.2 |
| 47 | 8 | 10 | 593.3 | Free Base | 51.4 ± 2.8 |
| 48 | 8 | 11 | 527.3 | Trifluoroacetate | 51.6 ± 1.8 |
| 49 | 8 | 12 | 503.2 | Trifluoroacetate | 60.6 ± 2.9 |
| 50 | 8 | 13 | 503.3 | Trifluoroacetate | 47.5 ± 3.4 |
| 51 | 8 | 14 | 606.2 | Trifluoroacetate | 42.5 ± 3.1 |
| 52 | 8 | 17 | 578.2 | Trifluoroacetate | 47.1 ± 4.7 |
| 53 | 8 | 20 | 570.2 | Trifluoroacetate | 51.3 ± 3.8 |
| 54 | 8 | 21 | 536.2 | Trifluoroacetate | 47.6 ± 3.0 |
| 55 | 8 | 22 | 536.2 | Trifluoroacetate | 44.9 ± 6.0 |
| 56 | 8 | 23 | 613.2 | Trifluoroacetate | 38.4 ± 3.3 |
| 57 | 8 | 24 | 591.3 | Trifluoroacetate | 36.8 ± 2.7 |
| 58 | 8 | 25 | 544.3 | Trifluoroacetate | 35.7 ± 0.8 |
| 59 | 8 | 26 | 562.3 | Trifluoroacetate | 44.3 ± 5.3 |
| 60 | 8 | 27 | 570.3 | Trifluoroacetate | 50.1 ± 2.7 |
| 61 | 8 | 28 | 545.3 | Trifluoroacetate | 64.6 ± 1.2 |
| 62 | 8 | 29 | 502.3 | Trifluoroacetate | 52.6 ± 3.8 |
| 63 | 8 | 30 | 545.3 | Trifluoroacetate | 69.9 ± 8.1 |
| 64 | 8 | 30 | 545.2 | Free Base | Not Tested |
| 65 | 8 | 31 | 537.2 | Trifluoroacetate | 54.7 ± 5.1 |
| 66 | 8 | 32 | 544.3 | Free Base | 43.5 ± 3.9 |
| 67 | 8 | 33 | 657.2 | Free Base | 58.7 ± 5.2 |
| 68 | 8 | 34 | 579.2 | Free Base | 66.0 ± 7.4 |
| 69 | 8 | 35 | 597.2 | Trifluoroacetate | 48.6 ± 5.1 |
| 70 | 8 | 36 | 598.2 | Trifluoroacetate | 52.5 ± 4.5 |
| 71 | 8 | 37 | 425.2 | Free Base | 46.5 ± 3.5 |
| 72 | 8 | 38 | 544.3 | Free Base | 74.7 ± 3.0 |
| 73 | 9 | 3 | 559.3 | Hydrochloride | 41.0 ± 5.7 |
| 74 | 9 | 5 | 559.3 | Hydrochloride | 50.8 ± 9.8 |
| 75 | 7 | 5 | 531.2 | Hydrochloride | 82.0 ± 2.5 |
| 76 | 7 | 30 | 531.2 | Hydrochloride | 71.4 ± 10.6 |

Alternate Preparation of Example 37

A 1 gallon autoclave is charged with the compound of Example 45 (105 g, 183 mmol) and methanol (1.2 L). The tank is pressurized with ammonia gas to 50 psig and the contents are heated to 40° C. After 66 hours the tank is cooled to 20° C., and the solution is filtered through celite and glass paper. The tank is rinsed with a total of 1.5 L of methanol and the combined filtrates are concentrated to a foam (105.41 g). MS (ES+) m/z 545.

Alternate Preparation of Example 38

The compound of Example 37 (160.20 g, 294.1 mmol) is solved in methanol (1.6 L). Concentrated hydrochloric (24.5 mL) is added and the resulting solution is heated to 60–65° C. Methyl-t-butylether is then added (1.2 L) over the course of 2.25 hours while maintaining reflux. When the addition is complete the mixture is allowed to cool to 21° C., at which point it is further cooled to <2° C. in an ice bath. The mixture is stirred for 1 hour and is then filtered. The solids are dried in a 50° C. vacuum oven to provide 133.61 g (78%) of crystalline solid. MS (ES+) m/z 545.

Alternative Preparation of Example 44

To a 3 neck, 3 L flask, Epoxide 8 (122 g, 469 mmol, 1 equivalent), Amine 7 (250 g, 797 mmol, 1.7 equivalents), and ethanol denatured with toluene (1.5 L, 12 vol.) is added. The reaction is heated to reflux and allowed to stir at reflux for 25 hours. The reaction is then concentrated in vacuum to oil. The oil is taken up in ethyl acetate (10 volumes, 2×) and stripped down to a glassy oil. The oil is then dissolved in ethyl acetate (10 volumes) and water (5 volumes). The two layers are separated and the resulting organic layer is washed with water (5 volumes based on product). The resulting organic layer is then washed with 1N aqueous hydrochloric acid/water (0.25 eq of acid based on excess amine). The organic layer is then checked, via HPLC, for any excess amine. If amine is detected the organic layer is washed with 1N aqueous hydrochloric acid/water (increments of 0.1 eq of acid) until all the amine is completely removed. The organic layer is washed with 1N aqueous sodium hydroxide (1 volume) and saturated sodium chloride (5 vol.), dried over magnesium sulfate, filtered, and stripped to a foam. The foam is chromatographed using 3 kg silica gel. Eluent consisted of 3A ethanol:tetrahydrofuran:heptane: dichloromethane (first 8 fractions, 3:6:31:60, next 5 4:8:28:60, last 5 fractions 7.5:12.5:20:60). MS (ES+) m/z 574.1.

Demonstration of Function

The genes encoding the human $\beta_1$-adrenergic receptor (Frielle et al., *Proc. Natl. Acad. Sci.*, 84:7920–7924, 1987), the human $\beta_2$-adrenergic receptor (Kobika et al., *Proc. Natl. Acad. Sci.*, 84:46–50, 1987, Emorine et al., *Proc. Natl. Acad. Sci.*, 84:6995–6999, 1987) and the human $\beta_3$ adrenergic receptor (Granneman et al., *Molecular Pharmacology*, 44(2):264–70, 1993) are individually subcloned into a phd expression vector (Grinnell et al., *Bio/Technology*, 5:1189–1192, 1987) and transfected into the DXB-11 Chinese hamster ovary (CHO) cell line by calcium phosphate precipitation methodology. The stably transfected cells are grown to 95% confluency in 95% Dulbecco's modified Eagles Medium (DMEM), 5% fetal bovine serum and 0.01% proline. Media is removed and the cells are washed with phosphate buffered (pH 7.4) saline (without magnesium and calcium). Cells are then lifted using an enzyme free cell dissociation solution (Specialty Media, Lavallette, N.J.) and pelleted by centrifugation.

Cells from each of the above cell lines are resuspended and added (20,000/well) to a 96-well plate. Cells are incubated at 37° C. with representative compounds of the invention for 20 minutes in buffer (Hank's balanced salt solution, 10 mM HEPES, 0.1% BSA, 1 mM L-ascorbic acid, 0.2% dimethyl sulfoxide, 1 mM 3-isobutyl-1-methylxanthine, pH 7.4). After halting the incubation with quench buffer (50 mM Na Acetate, 0.25% Triton X-100, pH 5.8), the c-AMP level is quantified by scintillation proximity assay (SPA) using a modification of the commercially available c-AMP kit (Amersham, Arlington Heights, Ill.) with rabbit anti-cAMP antibody (ICN Biomedicals, Aurora, Ohio) for the kit.

Sigmoidal dose response curves, from the whole cell receptor coupled c-AMP assay are fit to a four parameter logistic equation using non linear regression: $y=(a-d)/(1+(Dose/c)^b)+d$ where a and d are responses at zero and maximal dose, b is the slope factor and c is the $EC_{50}$ as previously described (DeLean et al., *Am. J. Physiol.*, 235, E97–E102, 1978). $EC_{50}$ is assessed as the concentration producing 50% of the maximum response to each agonist.

Isoproterenol is accepted in the art as a non-selective $\beta_3$ agonist and is widely used as a comparator in evaluating the activity of compounds. See *Trends in Pharm. Sci.*, 15:3, 1994. The % intrinsic activity ($E_{max}$) of representative compounds of the invention is assessed relative to isoproterenol by the compound's maximal response divided by the isoproterenol maximal response times 100.

In Vitro Rat Atrial Tachycardia

Male rats (250–350 g) (Harlan Sprague Dawley, Indianapolis, Ind., USA) are killed by cervical dislocation. Hearts are removed and the left and right atria are dissected and mounted with thread in tissue baths containing 10 mls of modified Krebs' solution. Initial resting tension is 1.5–2.0 g at the outset of the experiment (*Naunyn-Schmied Arch. Pharmacol.*, 320:145, 1982). Tissues are allowed to equilibrate approximately 30 minutes with vigorous oxygenation before exposure to a compound of the invention.

To evaluate the ability of test compounds to increase heart rate, representative compounds of the present invention are added cumulatively once the atrial rate reached a steady state from the previous addition. Compound addition is continued until no further increase in atrial rate occurred or until a concentration of $10^{-4}$M is reached. The increase in beats per minute (bpm) is measured for each concentration of test compound by means of a BioPac System (*Br. J. of Pharmacol.*, 126:1018–1024, 1999).

Relative to a compound of formula I where $R^1$, $R^{1a}$, $R^2$, $R^3$ and $R^4$ are hydrogen, $R^5$ and $R^6$ are both methyl, $X^2$ is O, and $R^7$ is 5-carboxamido-pyrid-2-yl (not claimed, generically disclosed in U.S. Pat. No. 5,786,356), corresponding compounds of the present invention exhibit a reduction in atrial tachycardia.

Utilities

As agonists of the $\beta_3$ recptor, a compound of the present invention is useful in treating conditions in human and non-human animals in which the $\beta_3$ receptor has been demonstrated to play a role. The diseases, disorders or conditions for which compounds of the present invention are useful in treating or preventing include, but are not limited to, (1) diabetes mellitus, (2) hyperglycemia, (3) obesity, (4) hyperlipidemia, (5) hypertriglyceridemia, (6) hypercholesterolemia, (7) atherosclerosis of coronary, cerebrovascular and peripheral arteries, (8) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (9) neurogenic inflammation of airways, including cough, asthma, (10) depression, (11) prostate diseases such as benign prostate hyperplasia, (12) irritable bowel syndrome and other disorders needing decreased gut motility, (13) diabetic retinopathy, (14) neuropathic bladder dysfunction, (15) elevated intraocular pressure and glaucoma and (16) non-specific diarrhea dumping syndrome.

In treating non-human, non-companion animals, the compounds of the present invention are useful for increasing weight gain and/or improving the feed utilization efficiency and/or increasing lean body mass and/or decreasing birth mortality rate and increasing post/natal survival rate.

Formulation

The compound of formula I is preferably formulated in a unit dosage form prior to administration. Therefore, yet another embodiment of the present invention is a pharmaceutical formulation comprising a compound of formula I and a pharmaceutical carrier.

The present pharmaceutical formulations are prepared by known procedures using well-known and readily available ingredients. In making the formulations of the present invention, the active ingredient (formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

FORMULATION EXAMPLES

| Formulation 1: Tablets | |
|---|---|
| Ingredient | Quantity (mg/tablet) |
| Active Ingredient | 5–500 |
| Cellulose, microcrystalline | 200–650 |
| Silicon dioxide, fumed | 10–650 |
| Stearate acid | 5–15 |

The components are blended and compressed to form tablets.

| Formulation 2: Suspensions | |
|---|---|
| Ingredient | Quantity (mg/5 ml) |
| Active Ingredient | 5–500 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

| Formulation 3: Intravenous Solution | |
|---|---|
| Ingredient | Quantity |
| Active Ingredient | 25 mg |
| Isotonic saline | 1,000 ml |

The solution of the above ingredients is intravenously administered to a patient at a rate of about 1 ml per minute.

Dose

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. However, it will be understood that the therapeutic dosage administered will be determined by the physician in the light of the relevant circumstances.

Generally, an effective minimum daily dose of a compound of formula I is about 5, 10, 15, or 20 mg. Typically, an effective maximum dose is about 500, 100, 60, 50, or 40 mg. Most typically, the dose ranges between 15 mg and 60 mg. The exact dose may be determined, in accordance with the standard practice in the medical arts of "dose titrating" the recipient; that is, initially administering a low dose of the compound, and gradually increasing the does until the desired therapeutic effect is observed.

Route of Administration

The compounds can be administered by a variety of routes including the oral, rectal, transdermal, subcutaneous, topical, intravenous, intramuscular or intranasal routes.

Combination Therapy

A compound of formula I may be used in combination with other drugs that are used in the treatment/prevention/suppression or amelioration of the diseases or conditions for which compounds of formula I are useful. Such other drug(s) may be administered, by a route and in an amount commonly used therefor, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I. Examples of other active ingredients that may be combined with a compound of formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;
(b) insulin or insulin mimetics;
(c) sulfonylureas such as tolbutamide and glipizide;
(d) alpha-glucosidase inhibitors (such as acarbose);
(e) cholesterol lowering agents such as
  i. HMG-CoA reductase inhibitors (lovastatin, simvastatin and pravastatin, fluvastatin, atorvastatin, and other statins),
  ii. sequestrants (cholestyramine, colestipol and a dialkylaminoalkyl derivatives of a cross-linked dextran),
  iii. nicotinyl alcohol nicotinic acid or a salt thereof,
  iv. proliferator-activator receptor a agonists such as fenofibric acid derivatives (gemfibrozil, clofibrat, fenofibrate and benzafibrate),
  v. inhibitors of cholesterol absorption for example beta-sitosterol and (acyl CoA:cholesterol acyltransferase) inhibitors for example melinamide,
  vi. probucol,
  vii. vitamin E, and
  viii. thyromimetics;
(f) PPARδ agonists such as those disclosed in WO97/28149;
(g) antiobesity compounds such as fenfluramine, dexfenfluramine, phentermine, sibutramine, orlistat, and other β3 adrenergic receptor agonists;
(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;
(i) PPARα agonists such as described in WO 97/36579 by Glaxo;
(j) PPARγ antagonists as described in WO97/10813; and
(k) serotonin reuptake inhibitors such as fluoxetine and sertraline.

We claim:
1. A compound of formula I:

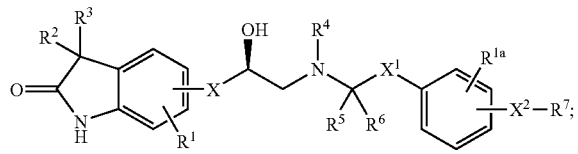

wherein:
$R^1$ is H, CN, halo, $C_1$–$C_6$ alkyl, $C_1$–$C_4$ haloalkyl, $CO_2R^8$, $CONHR^8$, $NHCOR^8$, $NHR^8$, $OR^8$, $SR^8$, $SOR^8$, $SO_2R^8$ or $SO_2NHR^8$;

$R^{1a}$ is H, halo or $C_1$–$C_6$ alkyl;

$R^2$ is H, $C_1$–$C_6$ alkyl or benzyl;

$R^3$ is $C_1$–$C_6$ alkyl or benzyl;

provided that if $R^3$ is $C_2$–$C_6$ alkyl or benzyl, then $R^2$ must be hydrogen;

$R^4$ is H or $C_1$–$C_6$ alkyl;

$R^5$ and $R^6$ are independently H or $C_1$–$C_6$ alkyl;

$R^7$ is hydrogen, optionally substituted phenyl or optionally substituted heterocycle;

$R^8$ is H or $C_1$–$C_6$ alkyl;

X is $OCH_2$, $SCH_2$ or a bond; and $X^1$ is a bond or a $C_1$–$C_5$ divalent hydrocarbon moiety; and $X^2$ is O, S, NH, $NHSO_2$, $SO_2NH$, $CH_2$ or a bond;

or a pharmaceutical salt thereof.

2. The compound of claim 1 wherein:
$R^1$ is H, CN, halo, $C_1$–$C_4$ alkyl, $C_1$–$C_4$ haloalkyl, $CO_2R^8$, $CONHR^8$, $NHCOR^8$, $NHR^8$, $OR^8$, $SR^8$, $SOR^8$, $SO_2R^8$ or $SO_2NHR^8$;

$R^{1a}$ is H, halo or $C_1$–$C_4$ alkyl;

$R^4$ is H or $C_1$–$C_4$ alkyl;

$R^5$ and $R^6$ are independently H or $C_1$–$C_4$ alkyl;

$R^7$ is hydrogen, phenyl or heterocycle wherein said phenyl or heterocycle is optionally substituted one to three times independently with hydroxy, oxo, nitro, phenyl, benzyl, $C_1$–$C_4$ alkoxy, $COR^8$, $NHCO(C_1$–$C_4$ alkyl), $NHCO$(phenyl), $NHCO$(benzyl), $OCO(C_1$–$C_4$ alkyl), $OCO_2R^8$ and $OCONR^8R^8$; and $R^8$ is H or $C_1$–$C_4$ alkyl; or a pharmaceutical salt thereof.

3. The compound of claim 2 wherein:
$R^1$ is H;
$R^{1a}$ is H;
$R^2$ and $R^3$ are both methyl;
$R^4$ is H;
$R^5$ and $R^6$ are independently H or methyl;
$R^7$ is phenyl, pyridyl, pyridazinyl or pyrimidinyl wherein said $R^7$ moieties are optionally substituted once or twice with chloro, cyano, $CONH_2$ or $CO_2CH_3$;
X is $OCH_2$ and is connected to the indole ring system at the 4-position of said system;
$X^1$ is $CH_2$; and
$X^2$ is O; or a pharmaceutical salt thereof.

4. The compound of claim 3 which is the hydrochloride salt.

* * * * *